US008211425B2

(12) United States Patent  
Winqvist et al.

(10) Patent No.: US 8,211,425 B2  
(45) Date of Patent: *Jul. 3, 2012

(54) METHOD FOR TREATING DISSEMINATED CANCER

(75) Inventors: Ola Winqvist, Uppsala (SE); Magnus Thörn, Uppsala (SE)

(73) Assignee: SentoClone International AB, Stockholm (SE)

( * ) Notice: Subject to any disclaimer, the term of this patent is extended or adjusted under 35 U.S.C. 154(b) by 867 days.

This patent is subject to a terminal disclaimer.

(21) Appl. No.: 12/158,687

(22) PCT Filed: Dec. 20, 2006

(86) PCT No.: PCT/EP2006/012305
§ 371 (c)(1),
(2), (4) Date: Nov. 4, 2008

(87) PCT Pub. No.: WO2007/071389
PCT Pub. Date: Jun. 28, 2007

(65) Prior Publication Data
US 2009/0081175 A1   Mar. 26, 2009

(51) Int. Cl.
*A01N 63/02* (2006.01)
*A61K 35/02* (2006.01)
*A61K 35/26* (2006.01)

(52) U.S. Cl. ............ 424/93.71; 424/534; 424/578

(58) Field of Classification Search .......... None
See application file for complete search history.

(56) References Cited

U.S. PATENT DOCUMENTS

| 4,478,815 | A | 10/1984 | Burchlel et al. |
|---|---|---|---|
| 5,767,065 | A | 6/1998 | Mosley et al. |
| 5,814,295 | A | 9/1998 | Martin et al. |
| 7,012,098 | B2 | 3/2006 | Manning et al. |
| 7,951,365 | B2* | 5/2011 | Winqvist et al. ............ 424/93.71 |
| 2002/0182730 | A1 | 12/2002 | Gruenberg |
| 2003/0129749 | A1 | 7/2003 | Gundersen et al. |
| 2003/0228635 | A1 | 12/2003 | Hu et al. |
| 2006/0104950 | A1 | 5/2006 | Okano et al. |
| 2007/0141026 | A1 | 6/2007 | Winqvist et al. |
| 2009/0022695 | A1 | 1/2009 | Winqvist et al. |
| 2009/0074714 | A1 | 3/2009 | Winqvist et al. |
| 2009/0123443 | A1 | 5/2009 | Winqvist et al. |
| 2009/0220472 | A1* | 9/2009 | Winqvist et al. ............ 424/93.71 |
| 2010/0015161 | A1 | 1/2010 | Winqvist et al. |

FOREIGN PATENT DOCUMENTS

| EP | 645147 A1 | 3/1995 |
|---|---|---|
| EP | 1408106 A1 | 4/2004 |
| JP | 7-179352 A | 7/1995 |
| JP | 2002-519019 A | 7/2002 |
| WO | 97/46256 A | 12/1997 |
| WO | 99/53949 A | 10/1999 |
| WO | 00/00587 A1 | 1/2000 |
| WO | 01/05433 A1 | 1/2001 |
| WO | 2004/012681 A1 | 2/2004 |
| WO | 2004/016154 A2 | 2/2004 |
| WO | WO 2004/032951 | 4/2004 |
| WO | WO 2004/045650 | 6/2004 |

OTHER PUBLICATIONS

Rudikoff et al, PNAS USA, 79:1979-1983 (1982).
Coleman et al, Research in Immunology, 145(1):33-36 (1994).
Burgess et al, Journal of Cell Biology, 111:2129-2138 (1990).
George et al, Trends in Immunology, 26(12):653-659 (2005).
Thörn et al, Cancer Causes control, 8(4):560-567 (1997).
Holmang et al, J. Urol. 158(2):389-392 (1997).
Sternberg, Annals of Oncology, 13:273-279 (2002).
Advanced Bladder Cancer Meta-Analysis Collaboration, Lancet, 361:1927-1934 (2003).
Bassi et al, J. Urol., 161(5):1494-7 (1999).
Cabanas, Cancer, 39:456-466 (1977).
Balch et al, J. Clin. Oncol., 19:3622-3634 (2001).
Sherif et al, J. Urol., 166(3):812-815 (2001).
Lipponen et al, Eur. J. Cancer, 29A(1):69-75 (1992).
Morales et al, J. Urol., 116(2):180-183 (1976).
Itano et al, Nature Immunology, 4:733-739 (2003).
Moll et al, Am. J. Pathol., 140(2):427-447 (1992).
Ochsenbein et al, Nature, 411:1058-64 (2001).
Velotti et al, J. Immunotherapy, 20(6):470-478 (1997).
Baner et al, Clin Chem, 51(4):768-775 (2005).
Haas et al, Cancer Immunol Immunother, 30(6):342-350 (1990).
Housseau et al, Int J Cancer, 71(4):585-594 (1997).
Dudley et al, J. Clin. Oncol., 23(10):2346-2357 (2005).
Nakagomi et al, Cancer Res, 53:5610-5612 (1993).
Finke et al, Cancer Res, 53(23):5613-5616 (1993).
Sherif et al, European Urology, 50(1):83-91 (Jul. 2006).
Cohen et al, Urol Clin North Am, 19(3):421-428 (1992).
Burnet, Prog Exp Tumor Res, 13:1-27 (1970).
Ratliff, J. Urol., 137(1):155-158 (1987).
Ratliff, J. Urol., 150(3):1018-1023 (1993). Marits et al.: "Detection of immune responses against urinary blader cancer in sentinel lymph noded". European Urology, S. Karger AG., Basel, CH, vol. 49. No. 1, 2006, 59-70, XP005236774, ISSN: 0302-2838.
Mesel-Lemoine Mariana et al.: "Initial depletion of regulatory 7 cells: the missing solution to preserve the immune functions of T lymphocytes designed for cell therapy". Blood, vol. 107, No. 1, 2006, 381-388, XP002394643.
Zhou Gang et al.: "Amplification of tumor-specific regulatory T cells following therapeutic cancer vaccines." Blood, vol. 107, No. 2, 2006, 368-636, XP002394644.
Chin C S et al.: "Sentinel node mapping identifies vaccine-draining lymph nodes with tumor-specific immunological activity", Annals of Surgical Onclology, Raven Press, New York, NY, US, vol. 9, No. 1, Jan. 2002, 94-103, XP002245222.
Annonymus: "35 Annual Meeting and 20th Summer School of the Scandinavian Society for Immunology, Aarhus, Denmark, Jun. 13-16, 2004". Scandinavian Journal of Immunology, vol. 59, No. 6, Jun. 2004, 609-637, XP002394737 & 35th Annial Meeting and 20th Summer School of the Scandinavian Society for Immunology; Aarhus, Denmark; Jun. 13-16, 2004. ISSN: 0300-9475, p. 637.

(Continued)

*Primary Examiner* — Michail Belyavskyi
(74) *Attorney, Agent, or Firm* — Porter Wright Morris & Arthur

(57) ABSTRACT

The present invention discloses an immunotherapeutic method for treating a patient suffering from a disseminated cancer by administering expanded tumour-reactive CD4+ helper and/or CD8+ T-lymphocytes obtainable from one or more metastasis-draining lymph nodes (metinel nodes) draining a metastasis. The method comprises identification of one or more metinel lymph nodes in a patient, resection of the one or more nodes and, optionally all or part of the metastases, isolation of metastasis-reactive T-lymphocytes from said lymph nodes, in vitro expansion of said metastasis-reactive T-lymphocytes, and administration of the thus obtained T-lymphocytes to the patient, wherein the T-lymphocytes are CD4+ helper and/or CD8+ T-lymphocytes.

24 Claims, 10 Drawing Sheets

OTHER PUBLICATIONS

Tanaka H et al.: "Depletion of CD4+CD25+ Regulatory cells augments the generation of specific immune T cells in tumor-draining lymph nodes", Journal of Immunotherapy, lippincott Wiliams & Wilkins, Hagerstown, MD, US, vol. 25, No. 3, May 2002, 207-217, XP008054211, ISSN: 1524-9557.
Lind D S et al.: "Expansion and tumour specific cytokine secretion of bryostatin-activated T-cells from cryopreserved axillary lymp nodes of breast cancer patients", Surgical Oncology, Blackwell Scientific Publ., Oxford, GB, vol. 2. No. 5, Oct. 1993, 273-282, XP008018621, ISSN: 0960-7404.
Sakaguchi Shimon: Naturally arising Foxp3-expressing DC25+CD3+ regulatory T cells in immunological tolerance to self and non-self., Nature Immunology, Apr. 2005. vol. 6, No. 4, Apr. 2005. 345-352, XP002394639, ISBN: 1529-2908.
Moore KL: "Clinically oriented anatomy", Baltimore: Williams & Wilkins. 1985. pp. 41-46.
Renkins EM: "Some consequences of capiiary permeability to macromolecules. Starling's hypothesis reconsidered". Am J Physiology. 1986. pp. H706-H710.
Farzad et al, Melanoma Research, 7(2):S59-S65 (1997).
Meijer et al, Proceedings of the American Association for Cancer Research, 42:683-684 (2001), Abstract.
Wedgewood Pharmacy (http://www.wedgewoodpharmacy.com/isosulfan/2004).
Meijer et al, J. Clin. Pharmacol, 441:81S-94S (Jul. 2001).
Santin et al, Am J. Obstet Gynecol., 183:601-609 (2000).
Kan et al, Biotherapy, 6:245-250 (1994).
Stratagene Catalog, p. 39 (1983).
Elliot et al, Current Opinion in Immunology, 13:625-633 (2001).
Martis et al, British Journal of Cancer, 94(10):1478-1484 (2006).
Tanis, Breast Cancer Research, 3:109-112 (2001).
Janeway et al, Immunobiology 5, Garland Science, 2001, Fig. A24.
Janeway et al, Immunobiology 5, Garland Science, 2001, Appendix III.
Harada et al, Immunology, 87:447-453 (1996).
Spits et al, J. Immunology, 139:1142-1147 (1987).
Hofman et al, J. Immunology, 141:1186-1190 (1988).
Perussia et al, J. Immunology, 149:3495-3502 (1992).
Biron, Immunity, 14:661-664 (2001).
Byers, CA Cancer J Clin, 49(6):353-361 (1999).
Okamoto et al, Cancer Immunol and Immunotherap, 40:173-181 (1995).
Dudley et al, Nature Reviews Cancer, 3:666-675 (2003).
Marincola et al, Trends in Immunology, 24(6):334-341 (2003).
Panelli et al, J. Immunology, 164(1):495-504 (2000).
Cochran et al, Mod. Pathol., 14(6):604-608 (2001).
Frisell et al, Eur. J. Surg., 167:179-183 (2001).
Leong et al, Annals of Surgical Oncology, 9(1):82-87 (2002).
Yamshchikov et al, Int. J. Cancer, 92:703-711 (2001).
Bowie et al, Science, 257:1306-1310 (1990).
Kaiser, Science, 31:1370 (2006).
Gura, Science, 278:1041-1042 (1997).
Dillmon, Expert Review of Anti-Cancer Therapy, 5(6):1041, Abstract (2005).
Hedfords et al, Scandinavian Journal of Immunology, 58:522-532 (2003).
Kim et al, Cancer, 86:22-30 (1999).
Ruttinger et al, Clinical and Experimental Metastasis, 21:305-312 (2004).
Chen et al, J. Experimental Medicine, 198:1875-1886 (2003).
Kursar et al, J. Experimental Medicine, 196:1585-1592 (2002).
Sutmuller et al, J. Experimental Medicine, 194:823-832 (2001).
Winter et al, Immunology, 108:409-419 (2003).
Rosenberg et al, Proceedings of the National Academy of Sciences, USA, 101:14639-14645 (2004).
Dahl, European Journal of Surgical Oncology, 31:381-385 (Jan. 28, 2005).
Saxton et al, Blood, 89:2529-2536 (1997).
Rosenberg et al, Journal of the National Cancer Institute, 85(8):622-632 (1993).
Karlsson et al.: "Detection of immune responses in sentinel nodes draining human urinary bladder cancer", Scandinavian Journal of Immunology, vol. 59, pp. 609-637 Abstracts, 1999.

* cited by examiner

METHOD FOR TREATING DISSEMINATED CANCER

FIELD OF THE INVENTION

The invention relates to an immuno-therapeutically method for treating patients suffering from disseminated cancer, by administering expanded tumour-reactive CD4+ helper and/or CD8+ T-lymphocytes obtainable from one or more metinel lymph nodes draining a metastasis, wherein the T-lymphocytes are not CD4+ CD25+$^{Hi}$ lymphocytes, i.e. the present invention does not cover regulatory T-lymphocytes.

BACKGROUND OF THE INVENTION

The lymph system contains a network of vessels that carry lymph, a colorless, watery fluid originating from interstitial fluid. The vessels transport excess fluids away from interstitial spaces in body tissue and return it to the bloodstream, while preventing backflow of the lymph fluid. The three main types of lymphatic vessels are lymph capillaries, lymphatics, and lymph ducts. Lymph capillaries join to form larger vessels called lymphatics or lymph veins. These resemble blood-conducting veins but have thinner walls and relatively larger lumen, and they have more valves. In the skin, lymphatics are located in subcutaneous tissue and follow same paths as veins. In the viscera, lymphatics generally follow arteries and form plexuses (networks) around them. At certain locations lymphatics enter lymph nodes. These are small, specialized organs that consist of lymphatic tissue. Lymph is filtered through at least one lymph node before entering the venous circulation (Moore). Lymph nodes act as filters, with an internal honeycomb of connective tissue filled with lymphocytes that collect and destroy e.g. bacteria and viruses. In the node, the lymph is in contact with the blood circulation and about half of the fluid is drained into the blood before it leaves the node via an efferent lymphatic vessel (Renkin). It is an increasingly accepted view that practically all spreading of malignant cells from epithelial tumours first occur through thin fenestrated lymph vessels (by an active mechanism—also used by white blood cells) before entering the general blood circulation via the lympho-venous connections in the lymph nodes. Clusters of lymph nodes are found in the armpits, groins, neck, chest, and abdomen.

Primary tumours or primary tumour areas drain to one or more so-called sentinel lymph nodes, where the sentinel node is defined as the first lymph node, or nodes, to receive lymphatic drainage from a tumour, also known as the "sentinel node concept". This is also the first site of metastasis and it has been shown in several solid tumour types that the risk of lymph node metastases is almost negligible if the sentinel node is free of tumour cells. The sentinel node can be identified during surgery by injection of a tracer or dye substance around the tumour. These substances are transported in the lymph capillaries and accumulate through phagocytosis by macrophages in the sentinel node(s), thus identifying the tumour draining lymph node(s). The present inventors have recently shown that the sentinel lymph nodes draining a primary tumour are a potential rich source for naturally tumour-reactive T-lymphocytes for in vitro expansion, as the sentinel nodes may contain a substantial amount of T-lymphocytes, that have been sensitized towards tumour-antigens and undergone in vivo expansion in the lymph nodes (Marits et al, manuscript; Karlsson et al, Eur J Urol, accepted).

However, up till now, it has not been known that sequential lymphatic drainage involving a certain individual lymph node applies to metastasis as well, i.e. that for a metastasis one or more lymph nodes draining the metastasis area can be detected.

DISCLOSURE OF THE INVENTION

A metastasis of a primary tumour is defined as a cancer resulting from the spread of a primary tumour. Metastasis depends on the cancer cells acquiring two separate abilities—increased motility and invasiveness. Cells that metastasize are basically of the same kind as those in the original tumour. If a cancer arises in e.g. the colon and metastasizes to e.g. the liver, the cancer cells in the liver are colon cancer cells. However, the cells have acquired increased motility and the ability to invade another organ.

Theoretically primary tumours originate from the cells present in the organ or tissue in which the tumour develops. As the cells in such organs or tissues already are connected to a preexisting lymphatic drainage system, lymph will be drained from the primary tumour through already existing lymph vessels. Up till now, no one has shown that the "sentinel node concept" of primary tumours also applies for metastases, i.e. that one or more first lymph node(s) to receive drainage from a metastasis, can be identified for a metastasis. It has not been shown by anyone that a metastasis induces lymphangiogenesis, and furthermore, it is not obvious that a metastasis will develop connections to the lymphatic system.

The present inventors have found that metastases in e.g. a lymph node or in an organ, such as, e.g., the liver or in a tissue, such as, e.g. mesenteric fat tissue, have developed connections to the lymphatic system and drains to lymph nodes, and that one or more so-called "metinel" lymph nodes, i.e. the first lymph node(s) to receive lymph drainage from a metastasis, can be identified.

Theoretically, spreading of tumour cells from metastases may take place via blood vessels formed by angiogenic activity triggered by the tumour. It is believed that the lymphatic system is rather well preserved since embryonic development and that it is developed independent of the vascular blood system. Therefore it was unexpected for the present inventors to find that metastases from solid epithelial tumours can be investigated with a similar technique as has been developed for various solid primary tumours to map the lymphatic drainage. While investigating lymphatic drainage from different types of metastases located in subcutaneous tissue, lymphatic tissue, intraabdominally and in internal organs the inventors have identified metastasis-draining lymph nodes (metinel nodes). The metinel nodes are individually located, and it is often not the nodes at the shortest anatomical distance from the metastasis that are the metinel nodes, i.e. the first nodes to receive lymphatic drainage from a metastasis.

Further analyses of such metinel lymph nodes by the present inventors have shown that they contain T-lymphocytes with specific activity towards the tumour cells in the corresponding metastasis. The present inventors have further shown that the T-lymphocytes obtained from metinel lymph nodes can be expanded and used for treatment of disseminated cancer diseases Accordingly, the present invention relates to a method for treating a patient suffering from a disseminated cancer, the method comprising
  i) identifying in a patient one or more metinel lymph nodes,
  ii) resecting the one or more nodes and, optionally all or part of the metastases,
  iii) isolating metastasis-reactive T-lymphocytes from said lymph nodes, iv) in vitro expanding said metastasis-reactive T-lymphocytes, v) administering the thus obtained T-lymphocytes to the patient, wherein the T-lymphocytes are CD4+ helper and/or CD8+ T-lymphocytes and not CD4+ CD25+Hi lymphocytes, i.e. the present invention does not cover regulatory T-lymphocytes.

Before going in to further details with the steps of the method of the invention, the following terms is be defined:

By the term "tumour-reactive T-lymphocytes" is intended to mean T-lymphocytes carrying a T cell receptor (TCR) specific for and recognizing a tumour antigen. Herein the term tumour-reactive T-lymphocytes also tend to cover T-lymphocytes carrying a TCR specific for and recognizing metastasis antigens. I.e. the terms tumour-reactive T-lymphocytes and metastasis-reactive T-lymphocytes are used interchangeable.

By the term "T helper cells" is intended to mean T-lymphocytes that promote adaptive immune responses when activated.

By the term "Th1 cells" is intended to mean T helper cells that promote cell mediated immune responses when activated, using cytokines such as IFN-gamma.

By the term "Th2 cells" is intended to mean T helper cells promoting humoral immune responses when activated, using cytokines such as IL-4.

By the term "CD4+ helper T-lymphocytes" is intended to mean T-lymphocytes that express CD4 but not the transcription factor FoxP3.

By the term "CD8+ T-lymphocytes" is intended to mean T-lymphocytes that express CD8.

By the term "regulatory T-lymphocyte" is intended to mean T-lymphocytes that suppress adaptive immune responses, expressing transcription factor FoxP3.

By the term "specific activation" of T-lymphocytes is intended to mean antigen specific and MHC restricted T-cell receptor mediated activation. In contrast the term "unspecific activation" of T-lymphocytes is intended to mean a general activation of all T-cells, regardless of T-cell receptor specificity.

The term "tumour-derived antigen" intends to cover tumour cells, a homogenate of a tumour, which homogenate may be denatured, or tumour proteins, polypeptides or peptides, e.g. in the form of purified, natural, synthetic and/or recombinant protein, polypeptide or peptide. Please note that the term tumour herein also tend to cover metastasis of a primary tumour. The tumour-derived antigen may be intact molecules, fragments thereof or multimers or aggregates of intact molecules and/or fragments. Examples of suitable polypeptides and peptides are such that comprises from about 5 to about 30 amino acids, such as, e.g. from about 10 to 25 amino acids, from about 10 to 20 amino acids or from about 12 to 18 amino acids. If peptides are used, a final molar concentration in the culture of from about 0.1 to about 5.0 µM, such as, e.g., from about 0.1 to about 4.0 µM, from about 0.2 to about 3.0 µM, from about 0.3 to about 2.0 µM or from about 0.3 to about 1.0 µM may be used. The tumour-derived antigen may be autologous or heterologous, i.e. arise from the patient to be treated or be obtained from another subject suffering from cancer. In the present Examples the inventors uses an autologous denatured tumour extract, however, as mentioned above, other sources of the tumour-derived antigen may also be feasible for use in a method according to the invention.

By the term "day 1 of the first phase" or e.g. "day 5 of the second phase" is to be understood the following: The day on which the lymphocytes are harvested is denoted day 0 (zero). Day 1 of the first phase is defined as the day where the expansion is initiated by addition of at least one substance having agonistic activity towards the IL-2 receptor, and maybe culture medium and/or tumour-derived antigen. The expansion phase i) may be initiated on day 0 (zero) or up till 2 days after harvest of the lymphocytes. The day on which the second phase is initiated by addition of tumour-derived antigen is throughout the text described as "day 1 of the second phase".

By the term "sentinel lymph node" is intended to mean the first lymph node(s) to receive lymphatic drainage from a tumour. Primary tumours or primary tumour areas drain to one or more so-called sentinel lymph nodes. The sentinel nodes are also the first site of metastasis and it has been shown in several solid tumour types that the risk of lymph node metastases is almost negligible if the sentinel node is free of tumour cells. The term "metinel lymph node" refers to the first lymph node(s) to receive lymphatic drainage from a metastasis or a metastases area.

The first step of the present method is the identification of one or more metinel lymph nodes draining the metastasis. As mentioned above, locating a metinel lymph node is not necessarily an easy task, as it is often not the lymph nodes at the shortest anatomical distances that are the first to receive drainage from the metastasis. However, as the present inventors have found that the metinel nodes contain a higher amount of tumour-reactive T-lymphocytes than lymph nodes further down the lymphatic system from the metastasis, or than unrelated lymph nodes, wherein the content of tumour-reactive T lymphocytes are substantially zero, the step i) of identifying the one or more metinel nodes are crucial for the method according to the invention.

One way of identifying the metinel lymph node is by injecting one or more lymph node locators into the patient, i.e. any substances suitable for locating a lymph node. Such locators are preferably pharmaceutically acceptable and/or biocompatible. The locators can either be affinity based or non-affinity based. Examples of affinity based lymph node locators are antibodies in whole or fragments, nanobodies, nucleic acids such as RNA, DNA, and PNA all of which can be in turn labelled using various detection modalities. Detection of affinity based lymph node locators can be done by labelling with tracers and dyes, such as, e.g., the ones mentioned below. Visualization is then made by i) radiological methods such as x-ray, computerized tomography, scintigraphy, positron emission technique after labelling with contrast generating substances, such as, e.g., iodine containing substances or radioactive substances such as, e.g. technetium-99m, ii) magnetic resonance imaging after labelling with magnetic or paramagnetic substances, such as e.g., gadolinium, magnetodendromers or iron oxide containing particle; iii) light in the IR-visible-UV spectra by labelling with dyes, fluorescent dyes or luminescent dyes for detection by the naked eye or photon detecting devices such as CCD or CMOS sensors.

Examples of non-affinity based lymph node locators encompass tracers and dyes. These substances are transported in the lymph capillaries and accumulate through phagocytosis by macrophages in the sentinel or metinel node(s), thus identifying the tumour or metastasis draining lymph node(s).

Examples of tracers are radioactive substances such as, e.g., technetium-99 for radioactive decay based detection with photon sensitive films or sensors such as PET detectors. Further on magnetic, paramagnetic or superparamagnetic substances, such as, e.g., gadolinium containing contrast agents, iron oxide particles, magnetic oxide particles, magnetodendrimers for magnetic resonance based detection, contrast agents, such as, e.g., iodine for radiological based detection such as, e.g., computerized tomography or regular X-ray may be used.

Examples of dyes encompasses e.g., azo dyes, bisazo dyes, triazo dyes, diaryl methan dye, triaryl methan dye, anthrachino dye, polycyclic aromatic carbonyl dyes, indigo dyes for visualization by luminescence, near infrared, fluorescence, UV and visible light. Further on dyes also encompass luminescent substances for luminescence based detection and fluorescent substances, such as, e.g., pico green, sybr green, red O oil, texas red for fluorescence based detection. Detection can depending on the chosen wavelengths be made either by the naked eyes or photon detecting devices such as CCD or CMOS sensors.

In one embodiment the dye has an emission maximum that permits visualization by the naked eye in normal light. In another embodiment the dye has an emission maximum that permits visualization by the naked eye in UV light.

Other examples of suitable dyes or tracers appear from WO 04/045650, which is hereby incorporated by reference.

Another, but far more time-consuming way to identify metinel nodes is to remove and investigate a selection of lymph nodes in the presumed metastasis draining area. A tumour extract from the metastasis of the actual patient could then be used to identify lymph nodes containing tumour-reactive T-lymphocytes by proliferating assays.

The lymph node locators are injected into the patient into, above, around, adjacent and/or under the metastasis. The locator will then spread through lymph vessels leading into the metinel lymph node(s), and the one or more nodes will start to get stained within a certain period of time, such as, e.g. within 5 min to 30 min, such as, e.g. within 5 min to 15 min after injection of the locator substance, where after the locator substance is imaged. As described above, imaging of the locator is of course dependent on the locator substance used.

If a dye having an emission maximum that allows visualization by the naked eye in normal light is used, such as, e.g. Patent Blue, the one or more metinel nodes are simply identified as the nodes, which are first to accumulate the colored dye, i.e. if Patent Blue is used, the surgeon will look for the lymph nodes first to accumulate a blue color.

The locators may be injected by a single injection or by multiple injections, such as, e.g., by two or more injections, by three or more injections, by four or more injections, by five or more injections or by six or more injections.

How to perform the injections of the lymph node locators is dependent on the location of the metastasis. The lymph node locators may be injected by a non-surgical procedure, i.e. a procedure that does not involve a surgical step, wherein a surgical step is defined as one including surgical operative procedures, i.e. involving incisions with an instrument. In the present context, an injection, i.e. the punctuation of the skin with a needle, is not considered a surgical step. Accordingly, by the statement that the lymph node locator may be injected by a non-surgical procedure is intended to mean that the lymph node locator may be injected into, above, around, adjacent and/or under the metastasis directly into or through the skin.

Examples of situations wherein the lymph node locators may be injected into or through the skin, is e.g. cases where the metastasis is located in the skin of the patient. In such situations the lymph node locator should preferentially be injected into the skin above the metastasis, or through the skin into, around, adjacent and/or under the metastasis. If the metastasis is located in the subcutaneous tissue of the patient, the lymph node locator should preferentially be injected into the skin above the metastasis, or through the skin into, around, adjacent and/or under the metastasis.

As mentioned above, the metinel lymph nodes may not always be placed at the shortest or most logical anatomical distance from the metastasis. As an example of this is the surprising identification of a metinel node distally and medially to a groin lymph node metastasis by the present inventors as described in the Examples herein. Based on the anatomy of the lymphatic system, the suspected location of a metinel lymph node to a lymph node metastasis in the groin would be either proximal in the skin or in the subcutaneous fat or deep in the pelvis along the iliac vessels.

Accordingly, as a metinel lymph node may be placed distant from the metastasis, it may in some cases be very beneficial to inject a lymph node locator without the need for surgery, as it may be very difficult to predict the position of such a metinel lymph node. In theory a metastasis in the groin may have a metinel lymph node in the armpit, i.e. it can be very difficult to predict the place in the body to perform the surgery to remove the metinel node. In a specific embodiment of the invention, the lymph node locator is a radioactive substance, such as, e.g. technetium-99m, which may be injected by a non-surgical procedure, and later imaged by performing a lymphoscintigraphy.

Sentinel nodes drain primary tumours, which are usually derived from an organ that a priori has its lymphatic drainage organized since foetal development for that specific individual. The drainage pattern may differ between individuals. The present inventors have found that metastases located at various locations (liver, mesenteric fat, lymph nodes, subcutaneous tissue, muscle etc) also have a lymphatic drainage with first-draining lymph nodes. The present inventors call these nodes "metinel nodes". Most likely they have connected to the lymphatics through the metastasis own capacity to produce lymphangiogenic factors (such as VEGF-C). We have identified tumour-reactive lymphocytes in these metinel nodes (which have undergone clonal expansion towards the metastasis) and we have shown that they can be expanded with retained immunologic characteristics and used for cellular immunotherapy.

The lymph node locators may also be injected involving a surgical procedure, i.e. a procedure that includes an incision. As examples of a situation where a surgical procedure may be included is where the metastasis is located so it cannot be reached by a needle through the skin, or where imaging of the locator through the skin and tissues is not possible.

In such cases, the surgeon will perform an incision in the area of the metastasis and subsequently, a lymph node locator may be injected directly into, above, around, adjacent and/or under the metastasis in order to identify the one or more metinel lymph nodes. Examples of situations where the injection of the lymph node locators may include a surgical procedure is e.g. if the metastasis is located in the intraabdominal area, in the parenchymatous organs, or in the deeper located lymph nodes of the patient.

Some times the identification of the metinel lymph nodes may involve injection of lymph node locators by a combination of a non-surgical and a surgical step. As an example of this a radioactive lymph node locator, such as, e.g., technetium-99m may be injected using a needle, i.e. without the need for surgery, and the accumulation of the locator, i.e. identification of the metinel node(s) may be performed using a gamma detector. This gives the surgeon an indication towards where the metinel nodes are located.

Later on, when the patient is undergoing surgery to have the metinel lymph nodes and at least part of metastasis removed, a colored dye such as, e.g., Patent Blue Dye may be injected. Furthermore, if there is a lapse of more than about 18 to 24 hours after the first injection, it might be beneficial to add one or more extra injections with radioactive tracer dependent on the half-life of the radioactive tracer (usually about 6 hours) in order to identify the metinel nodes during surgery.

After having located the one or more metinel lymph nodes by one or the other method, the surgeon will remove these in order to investigate whether the metinel lymph nodes contain any tumour cells, and in order to obtain a culture of metastasis-reactive T-lymphocytes.

The harvesting of lymphocytes from the one or more metinel lymph nodes may be performed by homogenizing the metinel lymph node material in order to obtain single cell suspensions of lymphocytes. The single cell suspensions may then be subjected to in vitro expansion in order to obtain metastasis-reactive T-lymphocytes.

In Vitro Expansion

The in vitro expansion step iii) of the method according to the invention comprises i) a first phase of stimulating tumour-reactive CD4+ helper and/or CD8+ T-lymphocytes with tumour-derived antigen together with at least one substance having agonistic activity towards the IL-2 receptor, to promote survival of tumour-reactive T-lymphocytes, and ii) a second phase of activating and promoting growth of tumour-reactive CD4+ helper and/or CD8+ T-lymphocytes, wherein the second phase ii) is initiated when the CD25 cell surface marker (IL-2R marker) is down-regulated on T-lymphocytes.

Phase i)

The purpose of the first phase i) is to obtain a culture comprising a substantially high ratio of tumour-reactive CD4+ helper and/or CD8+ T-lymphocytes. The first phase is to be considered a "nursing phase" where the tumour-reactive T-lymphocytes are brought to survive and divide. Depending on the source of the T-lymphocytes (starting material for the in vitro expansion method), they may have phased relatively harsh conditions, such as, e.g., suppression and inhibition by factors secreted by cancer cells.

The starting material for use in the expansion method is a mixture of lymphocytes obtained from lymph nodes draining a metastasis.

The T-lymphocytes to be expanded in culture can be obtained from the subject to be treated, i.e. the resulting specific tumour-reactive T-lymphocytes for administering may be autologous. However, the T-lymphocytes can also be obtained from a source other than the subject to be treated, such as, e.g. another subject suffering from a cancer. In such case the recipient and the expanded tumour-reactive T-lymphocytes are preferably immunologically compatible (or the recipient is otherwise made immuno-tolerant of the expanded tumour-reactive T-lymphocytes).

The starting material will most likely comprise a mixture of various lymphocytes, such as, e.g., T-lymphocytes, B-lymphocytes, antigen presenting cells, tumour-reactive T-lymphocytes and non-activated/non-reactive T-lymphocytes. In order to promote survival specifically of the tumour-reactive T-lymphocytes, tumour-derived antigen and one or more substances having agonistic activity towards the IL-2 receptor are added.

As mentioned above the first phase i) is initiated by adding at least one substance having agonistic activity towards the IL-2 receptor. The function of such substances is to stimulate T-lymphocytes via the IL-2 receptor to promote cell division of T-lymphocytes, thereby preventing cell death.

Antigen specific MHC restricted activation of T-lymphocytes promotes clonal expansion of the useful T-lymphocyte population specific for the recognition of tumour cells. On the contrary, unspecific activation of T lymphocytes will lead to the expansion of T lymphocyte clones recognizing irrelevant peptides without any relation to the recognition of tumour cells, thus the majority of unspecifically expanded T lymphocytes will not recognize the tumour.

The invention aims to promote specific activation and growth of tumour-reactive CD4+ helper and CD8+ T-lymphocytes. A specific activation against a certain tumour antigen enables the T-lymphocytes to have therapeutic effect when administered to a cancer patient with the same tumour type as the T-lymphocytes are activated against.

In one embodiment of the invention the substances having agonistic activity towards the IL-2 receptor are agonists. Examples of such substances include proteins, polypeptides, peptides, antibodies, affibodies, and fragments thereof, fusion proteins, synthetic and/or organic molecules, such as, e.g., small molecules, and natural ligands. In a preferred embodiment the substance is the natural ligand of the IL-2 receptor, namely IL-2.

If IL-2 is used it is preferentially added in a low dose in order to reduce lymphocyte apoptosis and to increase the population of CD4 positive tumour-reactive T-lymphocytes. In a specific embodiment of the invention, the low dose of IL-2 is from about 100 IU/ml culture medium to about 700 IU/ml culture medium, such as, e.g., from about 100 IU/ml culture medium to about 600 IU/ml culture medium, from about 100 IU/ml culture medium to about 500 IU/ml culture medium, from about 100 IU/ml culture medium to about 400 IU/ml culture medium, from about 100 IU/ml culture medium to about 300 IU/ml culture medium and from about 100 IU/ml culture medium to about 200 IU/ml culture medium. In a specific embodiment, the amount of IL-2 added is 240 IU/ml.

In case other substances, than IL-2, having agonistic activity towards the IL-2 receptor are used the specific doses of these should be such that lead to an effect corresponding to the effect obtained by the above-mentioned doses of IL-2.

A further amount of the at least one substance having agonistic activity towards the IL-2 receptor may be added regularly throughout phase i), such as, e.g., every $2^{nd}$, $3^{rd}$ or $4^{th}$ day of phase i), in order to maintain optimal conditions for promoting cell division. By the term every $2^{nd}$, $3^{rd}$ or $4^{th}$ is intended to mean that at least one substance having agonistic activity towards the IL-2 receptor is added throughout phase i) every $2^{nd}$, $3^{rd}$ or $4^{th}$ day, starting at the $2^{nd}$, $3^{rd}$ or $4^{th}$ day after the first addition of the at least one substances having agonistic activity towards the IL-2 receptor, i.e. after initiating phase i).

In one embodiment the substance to be added regularly throughout phase i) is an agonist of IL-2. In a preferred embodiment the substance is IL-2.

The further dose of substances having agonistic activity towards the IL-2 receptor, such as, e.g., IL-2, to be added regularly, such as, e.g. every $2^{nd}$, $3^{rd}$, or $4^{th}$ day lies within the ranges mentioned above.

A further important step in the first phase i) of expansion is the addition of tumour-derived antigen in order to promote cell division of T-lymphocytes expressing T lymphocyte receptors recognizing tumour antigens, i.e. tumour-reactive T-lymphocytes.

The optimal point of time to add the tumour-antigen is depending on the source of lymphocytes. When the lymphocytes originates from lymph nodes the lymphocytes may have been subjected to close proximity and immuno-suppression by tumour cells, and need incubation with a substance having agonistic activity towards the IL-2 receptor, such as, e.g., IL-2 for some days in order to promote the ability of the T-lymphocytes to respond with proliferation upon tumour antigen presentation. Accordingly, in such case the tumour-derived antigen is preferentially added from day 2 to and including day 5 of the first phase i), such as, e.g., on day 2, on day 3, on day 4 or on day 5.

The tumour-derived antigen, such as, e.g., a tumour homogenate, is likely to be endocytosed and processed by antigen presenting cells present in the starting material, such as, e.g., B-lymphocytes, dendritic cells and macrophages. In most cases the tumour-derived antigen will be presented by class II MCH molecules leading to cell division of $CD4^+$ tumour-reactive T-lymphocytes. However, by cross presentation antigens taken up by endocytosis may be processed and presented in the class I pocket resulting in activation of $CD8^+$ T lymphocytes. As stated above, one of the objects of the expansion method is to in some respect imitate the natural pathway of the patients own immune system, and to a certain degree let the components of the patients immune system determine whether $CD4^+$ or $CD8^+$ lymphocytes are generated, depending on whether antigen is presented by MCHI or MCHII. In most cases, the antigens will be presented by the class II MCH molecule leading to generation of $CD4^+$ T-lymphocytes, however, in some cases CD8+ T-lymphocytes are generated.

Phase ii)

The purpose of the second phase ii) is to activate and expand the tumour-reactive CD4+ helper and/or CD8+ T-lymphocytes obtained by phase i) and to obtain a specific sub-population of tumour-reactive CD4+ helper and/or CD8+ T-lymphocytes by directing them into a desired pathway.

The present inventors have found, that one way of determining the optimal point in time to initiate phase ii) is by monitoring the expression of the CD25 cell surface marker on the T-lymphocytes, in order to determine specifically when the T-lymphocytes are susceptible to re-stimulation. The present inventors have found that the second phase ii) should preferably be initiated when the expression of CD25 on T-lymphocytes is down-regulated. CD25 is an activation marker, indicating that the lymphocytes have received an activating signal. If the second phase is initiated when the expression of CD25 on the T-lymphocytes is high, meaning that the lymphocytes have already received a signal, cell death would occur.

The down-regulation of CD25 is defined as that a substantial part of the T-lymphocyte population express very few or essentially none CD25 markers. In a preferred embodiment the down-regulation of CD25 is defined as that less than 5% of the T-lymphocyte population expresses CD25, i.e. 95% or more of the T-lymphocytes in the culture does not express CD25 at all. The 5% or less of the T-lymphocytes expressing CD25 are most likely regulatory CD4+ T-lymphocytes which have a high permanent expression of CD25. In addition, the T-lymphocyte population should preferably express very few or essentially none FoxP3 markers, which are specific markers of regulatory T-lymphocytes. In a preferred embodiment the down-regulation of FoxP3 is defined as that less than 5% of the T-lymphocyte population expresses FoxP3, i.e. 95% or more of the T-lymphocytes in the culture do not express FoxP3 at all.

Besides CD25, there are also other markers, the expression of which is relevant to monitor in order to determine the optimal point in time to initiate the second phase. Examples of such markers are the early activation marker CD69, and MCHII, which is an activation marker for T-lymphocytes. As the expression of CD69 and MCHII indicates that the "activation program" of the T-lymphocytes is already turned on, meaning that the cells are not able to respond to additional stimuli, both of these markers should preferably be down-regulated before the second phase is initiated. The term down regulation may be defined as that less than 5-10% of the T-lymphocyte population expresses CD69 and/or MCHII.

In another embodiment of the present invention, anti-CD4 antibodies are used to separate T helper cells from possible tumour cells in the culture in the expansion in phase ii) of the expansion method.

In a further or yet another embodiment of the present invention, products such as Dynabeads® with anti-CD3 and anti-CD28 antibodies are used to promote the expansion in phase ii) of the expansion method. Use of Dynabeads® CD3/CD28 will provide lymphocytes with activation signals and could also be used for separation from possible tumour cells in the culture. Dynabeads® CD3/CD28 will bind to T lymphocytes expanded antigen specifically during phase i), where these cells now can be enriched magnetically. Since the initial antigen specific activation has initiated and led to clonal T lymphocyte expansion the Dynabeads® CD3/CD28 restimulation will further promote clonal expansion since phase i) does not support activation of unspecific T lymphocyte clones.

Even though the exact starting point of phase ii) will vary depending on when the lymphocytes has acquired the preferred expression of specific markers, the second phase ii) is most often initiated from day 17 to and including day 23 of the first phase i), such as, e.g. on day 17, on day 18, on day 19, on day 20, on day 21, on day 22 or on day 23. In other words, the point in time, where the lymphocytes expresses the preferred amount and combination of markers, is most often seen as being from day 17 to day 23 of the first phase i).

The expansion of the T-lymphocytes, i.e. phase i) and ii) will most often take place in a suitable culture medium. Preferably a serum-free medium or autologous serum is used in order to avoid the risk of transmitting diseases to the patient. Examples of suitable standard media include AIMV medium, RPMI 1640, DMEM and MEM. However, other media may also be used, comprising a suitable blend of amino acids, steroids, vitamins, growth factors, cytokines and minerals.

During the two phases of the expansion, the cells may be split into several culture vessels in order to maintain a suitable cell density in the cultures. The density of the T-lymphocytes in the expansion phases should preferably be from about 3 to about 6 million cells/ml of culture medium.

During expansion an exchange of culture medium with fresh medium, a step, which is denominated conditioning of the medium, may also be needed. The point of time to split cultures and to condition the medium may be determined based on the morphology of the cells and the cell culture density (which should not exceed about 6 million cells/ml), or the medium may contain a suitable indicator, such as, e.g., a phenol indicator. In case an indicator is included in the medium, the point of time to split cultures or condition medium may be based on the colour of the medium. If a phenol red indicator is used, the cells should be split or conditioned, when the medium turns yellow, indicating that the pH of the culture is turning acidic. A suitable schedule for conditioning the medium used in the present invention may be to exchange from ¼ to ½, such as, e.g., ⅓ of the medium every 3-9 days, such as, e.g. once a week.

Except for the specific conditions mentioned herein, for other parameters standard conditions for growth of lymphocyte cultures will be used, such as, e.g. a temperature of 37° C. and 5% $CO_2$.

As mentioned above, the second phase ii) is initiated by the addition of tumour-derived antigen as defined above to the T-lymphocytes for activating the tumour-reactive CD25-negative T-lymphocytes, in order to promote clonal expansion of tumour-reactive T-lymphocytes.

In a specific embodiment of the invention antigen presenting cells (APCs) are added to the T-lymphocytes together with the tumour-derived antigen. Antigen presenting cells (APCs) include leukocytes such as, e.g., monocytes, macrophages and lymphocytes, such as, e.g., B cells. These diverse cell types have in common the ability to present antigen in a form that is recognized by specific T lymphocyte receptors. The leukocyte preparation is isolated from, for example, blood, lymph fluid, bone marrow, lymphatic organ tissue or tissue culture fluid obtained from the patient to be treated. In a preferred embodiment the APCs cells are irradiated peripheral blood leucocytes containing antigen-presenting B-cells and/or monocytes. The amount of APCs added lies within the range of from about 0.5 million APCs/ml lymphocyte culture to about 5 million APC/ml lymphocyte culture, such as, e.g., from about 1 million APCs/ml lymphocyte culture to about 4 million APC/ml lymphocyte culture, from about 1 million APCs/ml lymphocyte culture to about 3 million APC/ml lymphocyte culture, or from about 1 million APCs/ml lymphocyte culture to about 2 million APC/ml lymphocyte culture.

Besides the addition of tumour-derived antigen to the T-lymphocytes in order to promote clonal expansion of tumour-reactive T-lymphocytes, the second phase ii) comprises the addition of specific components the function of which are to direct the expansion of the tumour-reactive T-lymphocytes towards the desired sub-population.

As mentioned above, the present invention provides a method for the generation of tumour-reactive CD4+ helper T-lymphocytes. CD4+ helper T-lymphocytes recognizes and binds tumour antigen when the antigen is associated with a major histocompatibility complex class II molecule. Activated CD4+ helper T lymphocytes secrete cytokines, proteins and/or peptides that stimulate other cells of the immune system, such as other lymphocytes. The most common cytokine secreted is interleukin-2 (IL-2), which is a potent T lymphocyte growth factor. Activated, proliferating CD4+ helper T-lymphocytes can differentiate into two major subtypes of cells, Th1 and Th2 cells, which are defined on the basis of specific cytokines produced. Th1 cells produce interferon-gamma and interleukin 12 (IL-12), while Th2 cells produce interleukin-4, interleukin-5 and interleukin-13. Th1 T-lymphocytes are believed to promote activation of cytotoxic T lymphocytes (Tc), NK cells, macrophages, and monocytes, all of which can attack cancer cells and generally defend against tumours.

T-helper (CD4+) lymphocytes of type Th1 and Th2 can differentiate into memory cells and effector cells. Memory T-helper (CD4+) lymphocytes are specific to the antigen they first encountered and can be called upon during a secondary immune response, calling forth a more rapid and larger response to the tumour-antigens. There is evidence in humans that lymphocytes survive at least 20 years; perhaps for life. Effector CD4+ T-lymphocytes are active cells producing cytokines and INF-gamma.

For an effective treatment of cancer, administration of tumour-reactive T-lymphocytes of the Th1 type is especially beneficial, as this type is believed to promote activation of cytotoxic T lymphocytes (Tc), NK cells, macrophages, and monocytes, all of which can attack cancer cells and generally defend against tumours. I.e. in a specific embodiment the invention relates to a method for generating tumour-reactive CD4+ helper T-lymphocytes, and in a further embodiment, the percentage of T-lymphocytes of the Th2 type generated by the present method is 30% or less, such as, e.g., 25% or less, 20% or less, 15% or less, 10% or less, 5% or less or 0%, i.e. at least 70% of the tumour-reactive CD4+ T-lymphocytes are of the Th1 type, such as, e.g. at least 75%, at least 80%, at least 85%, at least 90%, at least 95% or 100%.

Accordingly, the second phase may comprise the addition of a substance capable of up-regulating IL-12R on the T-lymphocytes. Up regulation of the IL-12R will increase the readiness of the T cell to receive and optimize the IL-12 cytokine activation resulting in maximal STAT-4 signalling and thus skewing the lymphocytes towards Th1 cells and IFN-γ production.

The substance(s) capable of up-regulating IL-12R on the T-lymphocytes may be substance(s) having agonistic activity towards an interferon receptor. In one embodiment of the invention the substances having agonistic activity towards the interferon receptor are agonists. Examples of such substances include proteins, polypeptides, peptides, antibodies, affibodies, and fragments thereof, fusion proteins, synthetic and/or organic molecules, such as, e.g., small molecules, and natural ligands. In a specific embodiment the substance is the natural ligand of the interferon receptor, namely an interferon, such as interferon-α.

The optimal point of time to add the substance(s) capable of up-regulating IL-12R on the T-lymphocytes, such as, e.g. a substance having agonistic activity towards an interferon receptor may be determined by measuring the level of IL-12 in the culture medium. The substance(s) should preferably be added when the level of IL-12 is at least 1 fold, such as, e.g., at least 2, at least 3 fold, at least 4 fold, or at least 5 fold increased as compared to the level of IL-12 on day 1 of phase ii). In most cases, such an increase in the level of IL-12 will be seen from day 2 to and including day 4 after initiating the second phase ii), such as, e.g. on day 2, on day 3 or on day 4.

In order to substantially avoid the generation of tumour-reactive T-lymphocytes of the Th2 type, the second phase may further comprise the addition of one or more substances capable of antagonizing development of Th2 type T-lymphocytes. Examples of such substances are substances capable of neutralizing the interleukins IL-4, IL-5, IL-10, and/or TGF-beta (the latter not being an interleukin) all four of which are required for the establishment of the Th2 cytokine profile and for down regulation of Th1 cytokine production.

Examples of such substances include proteins, polypeptides, peptides, soluble receptors, antibodies, affibodies, and fragments thereof, fusion proteins, synthetic and/or organic molecules, such as, e.g., small molecules, and natural ligands. In a specific embodiment the substances are selected from antibodies that binds to the interleukins, thereby neutralizing them, such as, e.g. anti IL-4 antibody, anti IL-5 antibody and/or anti IL-10 antibody, together with soluble receptors (such as, e.g. TGF-beta receptor 1 and 11) and binding proteins for TGF-beta (such as, e.g. LAP and/or LTBP).

The one or more substances capable of antagonizing development of Th2 type T-lymphocytes, such as, e.g., one or more substances capable of neutralizing IL-4, IL-5, IL-10 and/or TGF-beta may be added on day 1 of the second phase ii). However, as antibodies are expensive, the addition of antibodies can also be performed in a subsequent step after addition of the substance capable of up-regulating IL-12R on the T-lymphocytes, such as, e.g., one day, two days or three days after addition of the substance capable of up-regulating IL-12R on the T-lymphocytes.

The neutralizing substances should be added in an amount sufficient to neutralize the interleukins, such as, e.g., in a 10-100 fold (molar) excess of the amount of interleukin to be neutralized. When using antibodies, a final concentration of from about 2 to about 4 ng/ml culture medium will normally be needed. For other types of neutralizing substances, a final concentration, giving the same effect as the concentration mentioned for antibodies, should be used.

In order to maintain the suppression of the development of Th2 type T-lymphocytes a further amount of the one or more substance capable of antagonizing development of Th2 type T-lymphocytes, such as, e.g., one or more substance capable of neutralizing IL-4, IL-5, IL-10 and/or TGF-beta may be added regularly throughout phase ii), such as, e.g. every $2^{nd}$, $3^{rd}$ or $4^{th}$ day of phase ii). It is to be understood that by the term every $2^{nd}$, $3^{rd}$ or $4^{th}$ is intended to mean that at least one substance capable of antagonizing development of Th2 type T-lymphocytes is added throughout phase i) every $2^{nd}$, $3^{rd}$ or $4^{th}$ day, starting at the $2^{nd}$, $3^{rd}$ or $4^{th}$ day after the first addition of the at least one substance capable of antagonizing development of Th2 type T-lymphocytes.

Furthermore, as for phase i) a further amount of a substance having agonistic activity towards the IL-2 receptor, such as, e.g., an agonist may be added regularly throughout phase ii) such as, e.g., every $2^{nd}$ to $4^{th}$ day of phase ii), i.e. on the $2^{nd}$, $3^{rd}$ or $4^{th}$ day in order to maintain optimal conditions promoting cell division. The dose of the substance to be added regularly lies within the optimal ranges mentioned under phase i) for addition of substances having agonistic activity towards the IL-2 receptor, such as, e.g., IL-2.

In order to favour the generation of Th1 type tumour-reactive T-lymphocytes, the second phase ii) may comprise adding one or more substances promoting the development of Th1 type T-lymphocytes. Examples of such substances are substances having agonistic activity towards the IL-7, IL-12, IL-15 and/or IL-21 receptor. More specific, the substances may be agonists for the IL-7, IL-12, IL-15 and/or IL-21 receptor. Examples of such agonists include proteins, polypeptides, peptides, antibodies, affibodies, and fragments thereof, fusion proteins, synthetic and/or organic molecules, such as, e.g., small molecules, and natural ligands. In a specific embodiment the substances are the natural ligands of the IL-7, IL-12, IL-15 and/or IL-21 receptor, respectively, such as IL-7, IL-12, IL-15 and/or IL-21.

The effect of IL-12 is activating the IFN-gamma inducing STAT pathway by stimulating the IL-12R thereby promoting activation of Th1 lymphocytes. The function of IL-21 is to enhance proliferation, activation and development towards a Th1 type of T-lymphocytes.

Both IL-7 and IL-15 work by promoting homeostatic expansion of the T-lymphocytes, enhancing the enumeration of activated Th1 programmed T-lymphocytes.

The optimal point of time to add one or more substances promoting development of Th1 type T-lymphocytes is when the T-lymphocytes are susceptible to modification. If the substances are added when the T-lymphocytes are not susceptible to modification, the addition will have no effect, i.e. the development of Th1 type T-lymphocytes will not be favored. In order to determine the optimal point in time for adding substances promoting development of Th1 type T-lymphocytes, such as, e.g., substances having agonistic activity towards the IL-7, IL-12, IL-15 and/or IL-21 receptor, the production of INF-γ by the T-lymphocytes, may be monitored. In a preferred embodiment, the one or more substances promoting the development of Th1 type T-lymphocytes, such as, e.g., substances having agonistic activity towards the IL-7, IL-12, IL-15 and/or IL-21 receptor should be added when the level of IFN-gamma is increased as compared to the level of IFN-gamma on initiation of second phase ii).

In a specific embodiment, the increase in IFN-gamma level may be determined as at least a 1 fold increase in IFN-gamma level, such as, e.g., at least a 2 fold, at least a 3 fold, at least a 4 fold increase as compared to the level of IFN-gamma on initiation of the second phase ii). Often will such an increase can be correlated to that the content IFN-gamma in the culture medium should be at least 100 picogram/ml culture medium, such as, e.g. at least 150 picogram/ml culture medium, at least 200 picogram/ml culture medium or at least 250 picogram/ml culture medium.

When determining the optimal point in time to add substances promoting development of Th1 type T-lymphocytes, such as, e.g., substances having agonistic activity towards the IL-7, IL-12, IL-15 and/or IL-21 receptor, one may further look at the expression of the activation markers CD25 and CD69 on CD4+ T-lymphocytes, which markers should preferentially be up-regulated. By up-regulation is understood that at least about 40% to about 60% or more of the CD4+ T-lymphocytes should express CD25 and CD69 as compared to the expression of CD25 and CD69 on T-lymphocytes on day 1 of phase ii), showing that the T-lymphocytes have received an activating signal.

Normally the optimal point of time for adding the substances promoting development of Th1 type T-lymphocytes will fall subsequent to the steps of adding the substances capable of up-regulating IL-12R on the T-lymphocytes and the substances capable of antagonizing development of Th2 type T-lymphocytes. More specific the optimal point in time to add the substances promoting development of Th1 type T-lymphocytes will fall between day 5 to day 8 after initiating the second phase ii), such as, on day 5, day 6, day 7 or day 8.

In case IL-7, IL-12, IL-15 and/or IL-21 are added the concentration of each of these substances in the culture medium should lie within the range from about 150 IU/ml culture medium to about 300 IU/ml culture medium, such as, e.g. 250 IU/ml culture medium. When other substances than the specific ones mentioned is used, they should be added to the culture in final concentration, which leads to the same effect as the addition of IL-7, IL-12, IL-15 and/or IL-21 within the specific ranges mentioned will give.

As mentioned above, the present method is preferentially used for the expansion of T-lymphocytes in order to achieve CD4+ tumour-reactive T-lymphocytes of the Th1 type. One further aspect of the invention is that by using the method described herein for expanding tumour-reactive T-lymphocytes, a relatively high amount of T-lymphocytes of the memory type will be obtained. In treating cancer it is of course important that the patient to be treated receive a high amount of effector tumour-reactive CD4+ T-lymphocytes, as these—as mentioned above—promote activation of cytotoxic T lymphocytes (Tc), NK cells, macrophages, and monocytes, all of which can attack cancer cells and generally defend against tumours.

However, by at the same time administering a substantial amount of memory tumour-reactive CD4+ T-lymphocytes, the patient achieve up to life long protection towards recurrence of the tumour or metastasis of the primary tumour.

Accordingly, the present invention relates to a method for the preparation of memory T-lymphocytes. Normally, when a culture of tumour-reactive T-lymphocytes are expanded according to the present invention from about 35% to about 90% of tumour-reactive T-lymphocytes of the memory type, such as, e.g. from about 40% to about 90%, from about 50% to about 80% or from about 60% to about 70%, will be obtained. The present inventors speculates that the fact that the lymphocytes in phase i) are allowed to regenerated before tumour antigen is added, together with the relatively slow expansion phase leads to formation of a high ratio of memory lymphocytes to effector lymphocytes.

As mentioned above the expression of the cell surface activation markers CD25 and CD69 on the T-lymphocytes may be used for determining when to initiate important steps of the present method, such as, e.g., when to initiate the second phase ii). Accordingly, it may be beneficial to continuously monitor the expression of CD25 and CD69 throughout phase i) and phase ii), such as, e.g., every $2^{nd}$, every $3^{rd}$ or every $4^{th}$ day.

As one of the purposes of the present method is to obtain a high number of specific CD4+ tumour-reactive T-lymphocytes, which may be used for administering to a patient, the tumour-reactive T-lymphocytes may be harvested at some point, leading to the termination of the expansion step. The optimal point of time to harvest the tumour-reactive T-lymphocytes is when the expression of CD25 on the T-lymphocytes is down-regulated, where the down-regulation is defined as that 5% or less of the CD4+ T-lymphocyte population expresses CD25. The optimal point in time to harvest may also be determined based on measurement of the amount of IFN-gamma produced. The IFN-gamma production should be at least 2 fold increased, such as, e.g., at least 3 fold, at least 4 fold or at lest 5 fold increased as compared to initial IFN-gamma production, which normally correspond to a level of IFN-gamma of at least 100 pg/ml of culture medium.

Normally, this event will occur from day 10 to and including day 14 after initiating the second phase ii), i.e. normally the cells will be harvested from day 10 to and including day 14 after initiating the second phase ii).

Accordingly, the entire process for expansion of tumour-reactive T-lymphocytes according to the invention may in general take from about 25 days to and including about 45 days, such as, e.g. from about 26 days to and including about 44 days, from about 27 days to and including 43 days, from about 27 days, to and including 42 days, from about 27 days to and including 41 days, and from about 27 days to and including about 40 days.

Instead of harvesting the tumour-reactive T-lymphocytes when the CD25 marker is down regulated, they may be subjected to one or more additional rounds of phase ii). This could be beneficial to do if the amount of tumour-reactive T-lymphocytes obtained by the expression method is not considered an effective amount to be administered to a patient suffering from cancer, or if the patient is in a chemo-therapy treatment regimen, where it may be considered beneficial to postpone the administration of T-lymphocytes until the chemotherapy treatment is finished. In order to determine whether the tumour-reactive T-lymphocytes should be subjected to one or more additional rounds of phase ii) one may look at the level of IFN-gamma produced, and/or the total number of tumour-reactive T-lymphocytes obtained and/or the expression of CD25. In the case the IFN-γ levels is 30 pg/ml culture medium or less, such as, e.g. 20 pg/ml culture medium or less, and/or the total number of T cells are unsatisfactory, additional rounds of phase ii) may be initiated beginning when the majority of T cells are CD25 negative (i.e. less than 5% of the T-lymphocytes population express CD25) and thereby susceptible to restimulation.

After harvest the tumour-reactive T-lymphocytes may be purified by any conventional means, such as, e.g. by using density gradient, such as, e.g., a Ficoll medium. A portion of the tumour-reactive T-lymphocytes may be stored by freezing in a suitable freezing medium after harvesting and purifying the tumour-reactive T-lymphocytes.

Method of Treatment

The tumour-reactive T-lymphocytes obtained by an improved expansion method are used herein for treating patients suffering from a disseminated cancer.

The definition of an effective amount of tumour-reactive T-lymphocytes to be administered is depending on the specific type of lymphocytes, the ratio of memory to effector T-lymphocytes and on the severity of the disease. However, in average a minimum of at least 10 million, such as, e.g. at least 20 million, at least 30 million, at least 40 million, at least 50 million, at least 60 million, at least 70 million or at least 80 million tumour-reactive T-lymphocytes may be administered. The present inventors have not identified any upper limit with respect to the amount of tumour-reactive T-lymphocytes to be administered in a single dose.

In a preferred embodiment the tumour-reactive T-lymphocytes for administration comprises a combination of effector T-lymphocytes and memory T-lymphocytes. More specific the amount of tumour-reactive T-lymphocytes of the memory type may be from about 35% to about 90%, such as, e.g. from about 40% to about 90%, from about 50% to about 80% or from about 60% to about 70%, and a percentage of effector T-lymphocytes from about 10% to about 65%, such as, e.g., from about 20% to about 50% or from about 30% to about 40%.

The tumour-reactive T-lymphocytes may be formulated as a pharmaceutical composition suitable for parenteral administration to the patient such as, e.g., intravenous, intraarterial, intrathecal, or intraperitonal administration.

When the tumour-reactive T-lymphocytes are administered parenterally, they may be formulated in an isotonic medium, i.e. in a medium having the same tonicity as blood, and comprising one or more substances preventing aggregation of the cells. A specific example of a suitable medium is a 0.9% NaCl solution comprising up to 3% human serum albumin such as, e.g. up to 2% human serum albumin or up to 1% human serum albumin. For intravenously administration the concentration of tumour-reactive T-lymphocytes in the composition to be administered normally lies within the range from about 0.5 million lymphocytes/ml medium to about 4 million lymphocytes/ml medium, such as, e.g., from about 0.5 million lymphocytes/ml medium to about 3 million lymphocytes/ml medium, from about 0.5 million lymphocytes/ml medium to about 2 million lymphocytes/ml medium or from about 1 million lymphocytes/ml medium to about 2 million lymphocytes/ml medium.

The composition comprising tumour-reactive T-lymphocytes may be administered as a single dose or multiple doses. It may be infused over 1 to 2 hours.

The treatment method may be performed once or repeated depending on the severity of the disease. Furthermore, the treatment may be reiterated upon recurrence of the disease.

The treatment according to the present invention may be supplemented with any other relevant treatment for disseminated cancer. Such supplemental treatment may be given before, at the same time or after the administration of the lymphocytes and it may be given at frequencies normally used for such treatments. A suitable example of supplemental treatment is chemotherapy and the like.

Kits

The invention further relates to kits for use in a method according to the invention, the kit comprising a medium for cultivation of T-lymphocytes. The medium may be any suitable serum-free medium, such as, e.g., AIMV, RPMI 1640, DMEM or MEM.

The kit may further comprise one or more substances for stimulating, activating and directing tumour-reactive T-lymphocytes. Examples of such substances may be tumour-derived antigen, substances having agonistic activity towards the IL-2 receptor, substances capable of up-regulating IL-12R on the T-lymphocytes, substances capable of antagonizing development of Th2 type T-lymphocytes and/or substances promoting the development of Th1 type T-lymphocytes.

More specific, such substances may be IL-2, interferon-alpha, anti-IL-4 antibody, anti-IL-5 antibody, anti-IL-10 antibody, IL-7, IL-12, IL-15 and/or IL-21.

The kit may also comprise a pharmaceutical composition suitable for intraavenous administration. The pharmaceutical composition may be mixed with the population of tumour-reactive T-lymphocytes before administration.

The kit may also comprise one or more syringes and a lymph node locator. In one embodiment, the syringes are prefilled with a lymph node locator.

The kits may also comprise instructions for use, such as, e.g. instructions in the form of computer software.

FIGURE LEGENDS

Figure 3A:
Figure 3B:

FIG. 3 illustrates identification of a tumour draining lymph node. FIG. 3 A shows how blue dye is injected around a tumour and how the dye is transported in the lymph capillaries, thus indicating the lymphatic drainage (indicated by white arrow). FIG. 3 B shows how a tumour draining lymph node has turned blue a few minutes after injection of the dye. White arrow indicates tumour draining lymph node.

Figure 4:
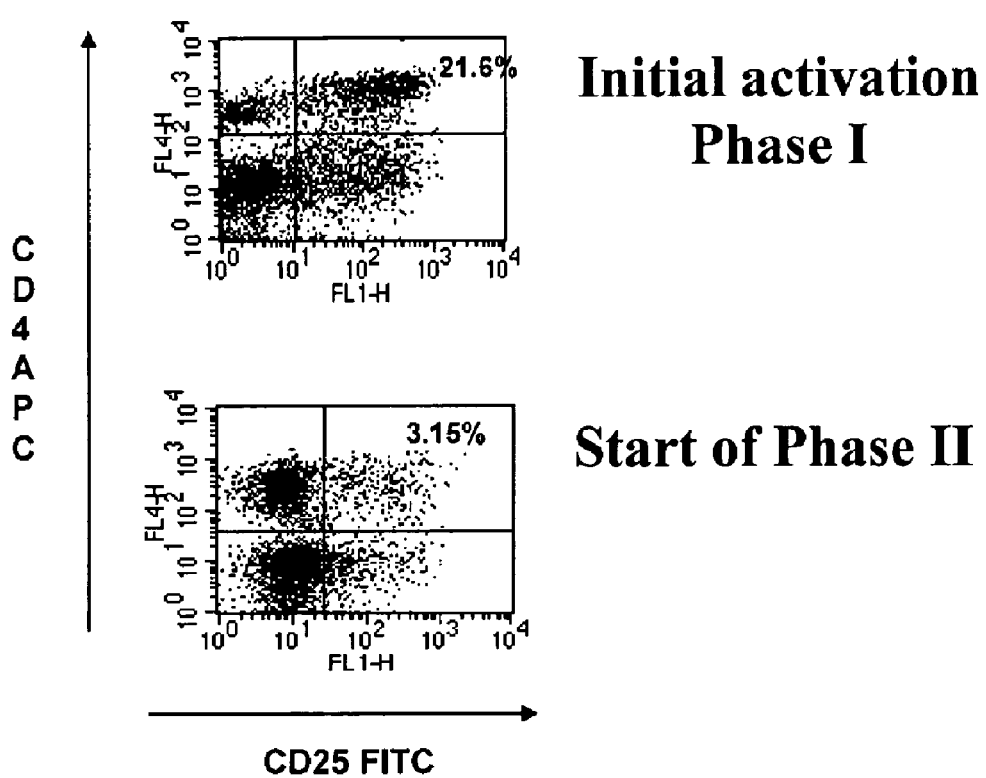

FIG. 4 shows that initially sentinel node lymphocytes are activated with tumour antigen and low dose IL-2 resulting in activation and expression of the activation marker CD25 (Top panel). The end of phase I activation phase is defined by the decreased number of CD4+ T cells expressing CD25 (Bottom panel). When less than 5% of the CD4+ T cells express CD25 phase II is initiated with restimulation with antigen.

Figure 5:
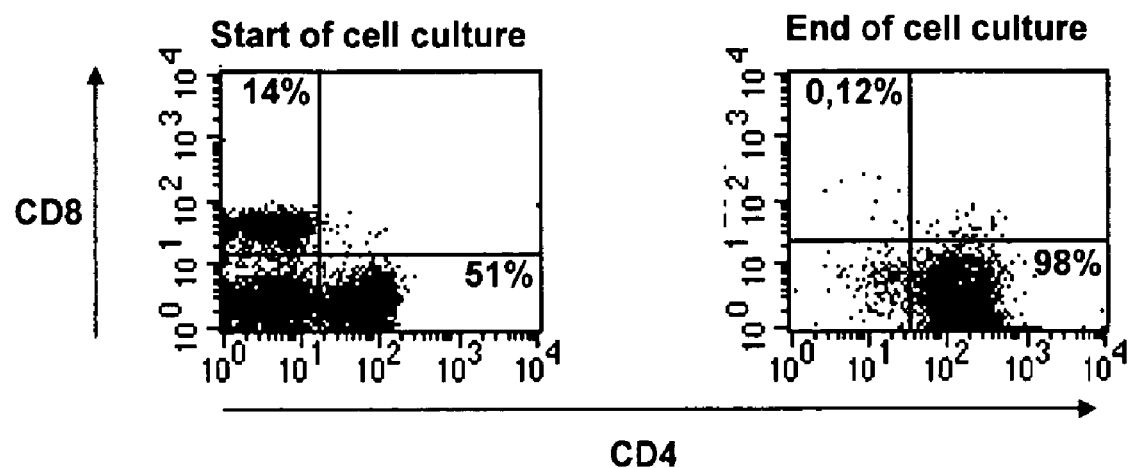

FIG. 5 illustrates that Phase I and Phase II activation results in expansion and enrichment of CD4+ T helper cells.

Figure 6:
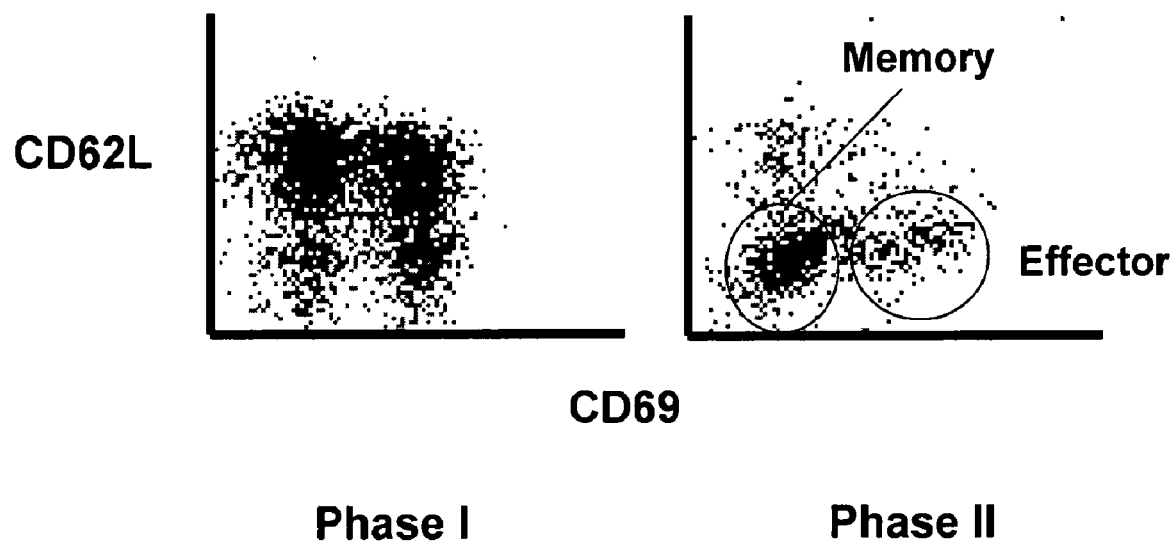

FIG. 6 illustrates that in Phase I the majority of cells are naïve CD62L+ cells or activated CD69+CD62L+ cells. After Phase II the majority of the cells is CD62L− and are composed of memory and effector CD4+ T helper cells. CD62L− T cells are not expressing the preferred lymph node homing molecule, thus they are seeking inflammatory areas in non lymphatic organs.

Figure 7:
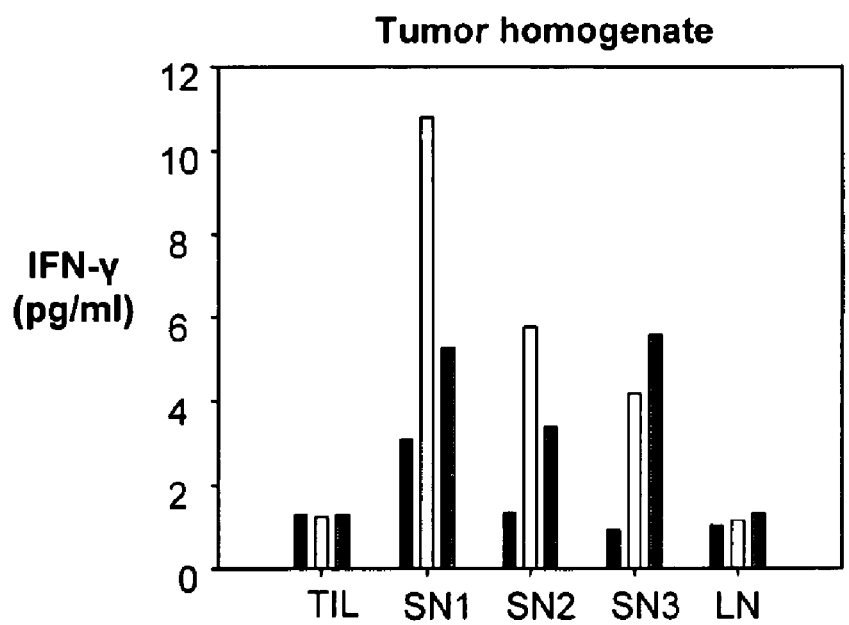

FIG. 7 shows primary cells stimulated in Phase I from tumour (Tumour infiltrating lymphocytes), metinel nodes (SN) and an irrelevant lymph node (LN) results in no or little IFN-γ production.

Figure 8:
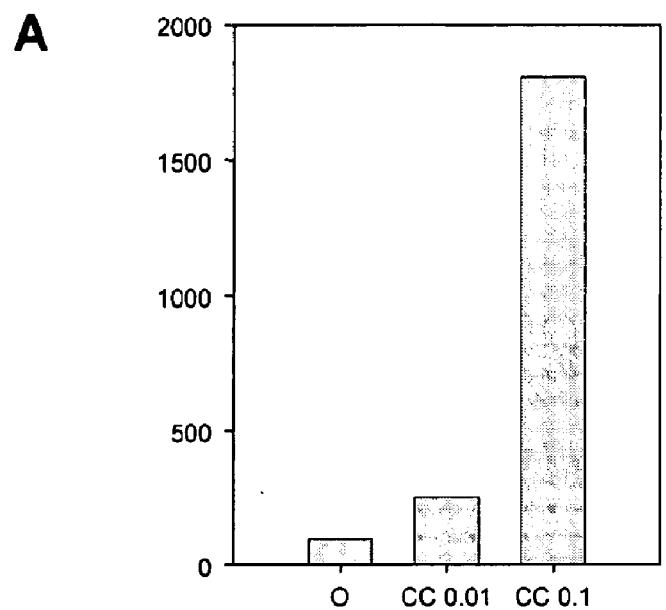
Figure 8:
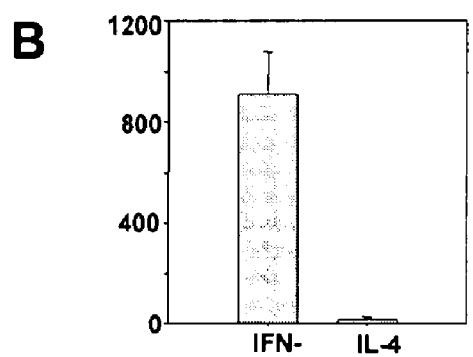

FIG. 8 illustrates that after expansion after phase ii) there is a dose dependent increase in antigen dependent IFN-γ production.

Figure 9:
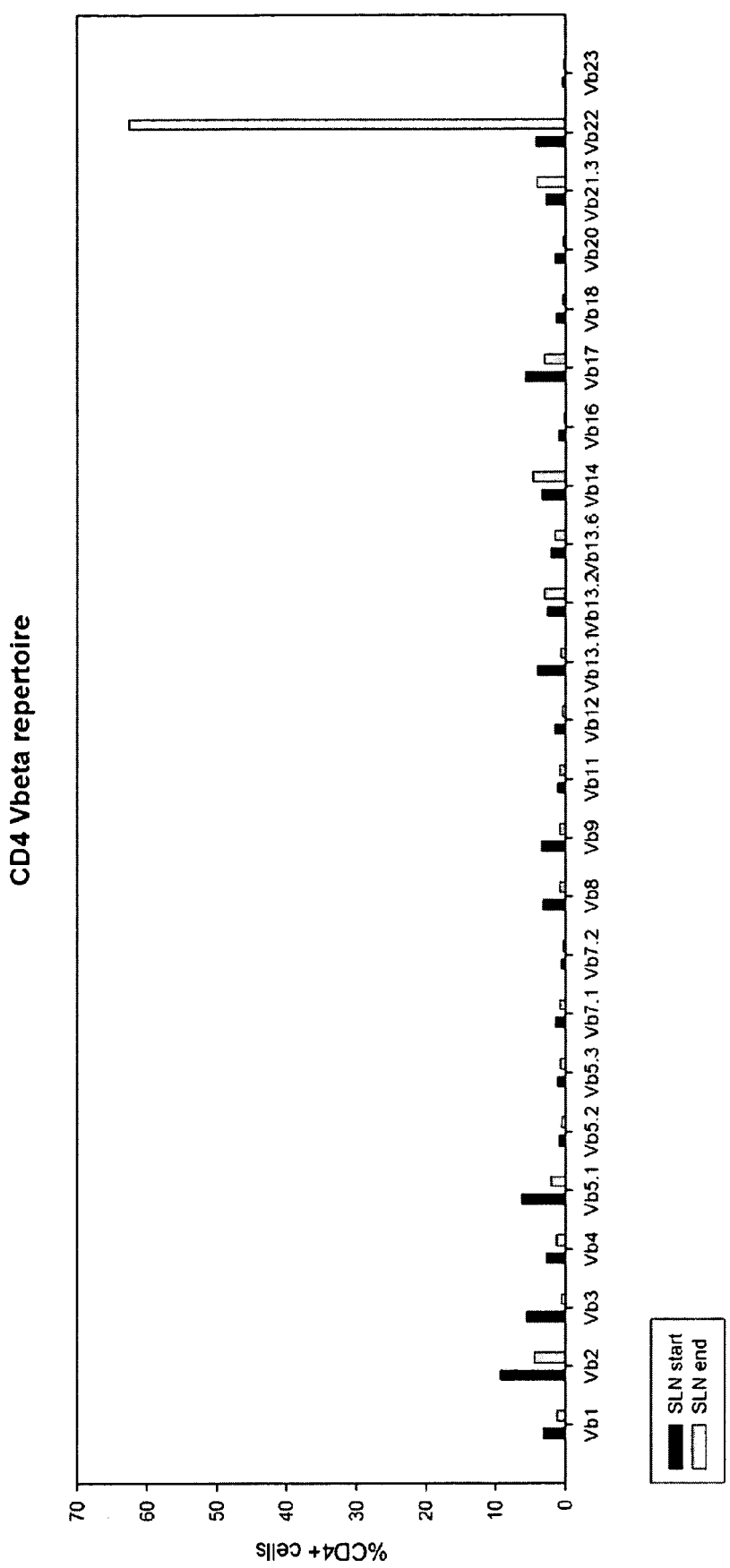

FIG. 9 illustrates that the expansion and activation protocol promotes the expansion of antigen specific T cell clones as investigated by the selective enrichment of TCR Vβ expression.

The following examples tend to illustrate the invention without limiting it in any way.

EXAMPLES

Example 1

Identification of Metinel Lymph Nodes for Metastasis

Eight patients (four women and four men) were included in the study (see Table 1); the average age was 61.4 years. One of them underwent two operations with localisations of metinel nodes at both procedures. Metinel nodes were located by three principally different ways. A lymph node locator was injected around and close to abdominal recurrences, parenchymatous liver metastases, or groin lymph node metastases.

TABLE 1

Overview of patients in study

| Patient no. | Years old | Sex | Primary tumour site | Origin of metinel nodes | Number of metinel nodes | Pos/Neg for metastatic disease |
|---|---|---|---|---|---|---|
| 1 | 48 | M | Caecum | Local recurrence | 3 | Pos |
| 2 | 54 | M | Rectum | Liver metastases | 2 | Neg |
| 3 | 77 | F | Colon sigmoideum | Liver metastases | 3 | Neg |
| 4 | 73 | M | Colon ascendens | Liver metastases | 4 | Neg |
| 5 | 66 | M | Colon ascendens | Liver metastases | 4 | Neg |
| 6 | 51 | F | Ovarian cancer | Liver metastases | 3 | Pos |
| 7 | 63 | F | Ovarian cancer | Groin lymph node metastases | 2 | Pos |
| 8 | 59 | F | Pancreatic cancer | Local recurrence | 4 | Pos |

The first patient was a 48-year old man who had earlier been operated on for a caecal cancer with a right-sided hemicolectomy. One year later he developed a 5 cm large intraabdominal recurrence in the mesenteric fat alongside the area of the anastomosis. A resection of the anastomotic region and the recurrence was made en bloc. Patent blue dye was injected around the metastasis and three metinel nodes along the medial colic artery, including one apical node in the root of the mesentery, were identified.

The second patient was a 54 year old man who had been operated on for a rectal cancer with an abdominoperineal rectal amputation and despite no distant metastases at investigation before surgery, the present inventors found a liver metastasis in the left liver lobe. CT scan of the abdomen was done postoperatively, the metastasis had an exterior diameter of three centimetres and was located between the second and third liver segment. Two months later he was operated with a partial left-sided liver resection and patent blue dye was injected in the parenchyma of the liver around and close to the metastasis. After about five minutes two metinel nodes were found in the hepatoduodenal ligament. Intraoperative ultrasound could not demonstrate any further metastases in the liver. No tumour cells were present in the metinel nodes; however the lymphocytes in the metinel node showed specific activity towards the metastasis.

Despite initial treatment with tumour-reactive lymphocytes and good general condition he developed a new liver metastasis in the right liver lobe and a second liver resection was done. At this operation injection of patent blue dye around the 2 cm large metastasis identified 2 metinel nodes located in the hilus of the liver.

The third patient was a 77-year old woman who two years earlier had been operated on for a sigmoid cancer with a sigmoid resection. At follow-up an elevated CEA was found and further investigations with PET-scan and CT-scan showed a four centimetres metastasis in the right liver lobe in between segment VI and VII. A subtotal right-sided hemihepatectomy was performed and after injection of Patent blue dye three metinel nodes were found at the liver hilus.

Patient number four was a 73-year old man who had been operated on for a tumour in the sigmoid colon with a sigmoid resection. More than one year later he developed a solitary liver metastasis of two centimetres in size and was operated with a partial resection of segment V and VI. After the injection of in total 1.0 ml Patent blue dye at four different locations around and close to the metastasis, one metinel node was identified in the liver hilus. Analysis of the node proved it to be without signs of metastatic disease but it contained tumour-reactive lymphocytes.

Patient number five was a 66-year old man who previously was operated on due to a cancer in colon ascendens with a right-sided hemicolectomy. CT-scan in a routine follow-up after surgery for colon cancer showed a 2.5 centimetres solitary metastasis in the right liver lobe, segment VII. At surgery 1.0 ml Patent blue dye was injected in the liver tissue around the metastasis and two metinel nodes were located in the hepatoduodenal ligament and two in the liver hilus. Resection of segment VI-VII was done together with extirpation of metinel nodes.

The 6$^{th}$ case was a 51 year old woman who six years earlier had been operated with a hysterectomy and bilateral salpingoophorectomy due to ovarian cancer. After that the cancer had disseminated to the abdomen and peritoneum and only palliative treatment remained. She had large, partly necrotic, liver metastases. At surgery three metinel nodes were identified central in the abdomen after injecting Patent Blue Dye adjacent to the liver metastases. The metinel nodes all contained tumour cells and tumour-reactive lymphocytes.

Figure 1:
FIG. 1 is a lymphoscintigraphy showing a metinel node distally and medially to the groin lymph node metastasis.
Figure 1:
Figure 2:
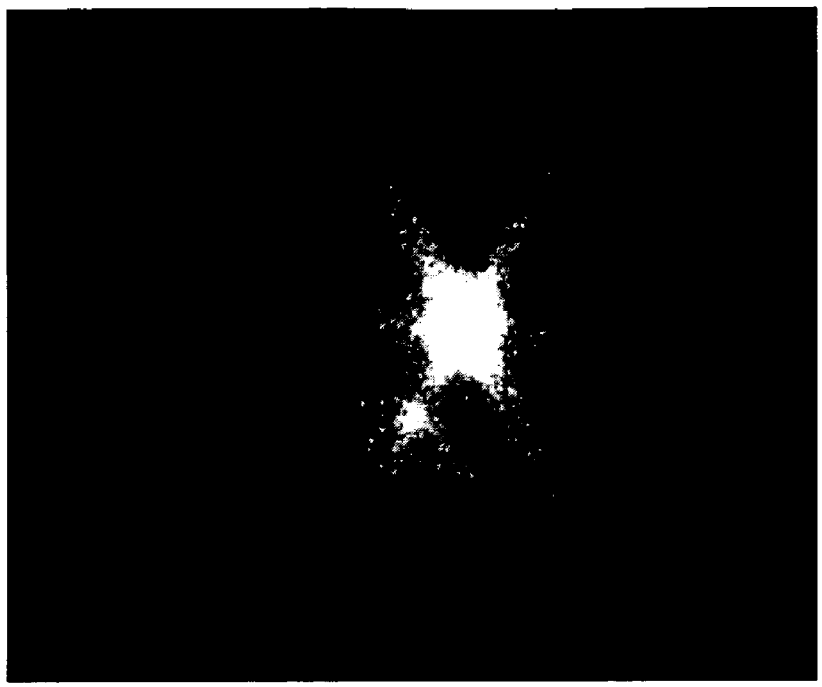
FIG. 2 is a lymphoscintigraphy showing a metinel node distally and medially to the neck lymph node metastasis.
Figure 2:

Patient number seven was a 63-year old woman who had been operated on for ovarian cancer with bilateral oophorectomy. At surgery she had disseminated disease to the omentum and underwent after this several tumour-reducing operations, including resection of the right colon due to a metastasis. One year further she developed a resistance in the left groin and a fine needle biopsy proved a metastasis from ovarian cancer. After injection of the tracer technetium-99 subcutaneously at four places (4×0.25 ml, 50 MBeq/ml) around the palpable metastasis the lymphoscintigraphy surprisingly demonstrated two metinel nodes closely together distally and medially to the groin lymph node metastasis (see FIG. 1). This node was further identified as a blue-colored metinel node draining the metastasis by injecting Patent blue dye at the same places as the tracer during the surgical procedure a few hours after the lymphoscintigraphy.

The 8$^{th}$ patient was a 59 years old woman who had been operated on with Whipples operation due to a pancreatic cancer. Two years later a local recurrence is diagnosed and she was operated with a tumour-reducing operation in which 4 metinel nodes were found, after injection of Patent blue dye adjacent and above the local recurrence.

Cytokeratin antibodies were used to detect malignant cells. Lymphocytes in nodes without metastases were spontaneously activated as shown by their ability to secrete interferon-gamma upon stimulation by tumour homogenate in proliferation assays. Lymphocytes from metastatic metinel nodes responded at first poorly to this stimulation, suggesting that they were immunosuppressed by the metastasis. However, cells from both non metastatic and metastatic nodes could be expanded to high numbers in vitro as described in Example 2.

Example 2

Expansion of Tumour-Reactive T-Lymphocytes

Identification of metinel nodes was done using the method described herein.

The metinel- and non-metinel lymph nodes were cut in half and one part of the node was sent for histopathological examination according to routine procedure. A part of the metastasis including a sample of the invasive margin was removed to use as an antigen source during the further procedure.

Cell Culture
Phase I, Initial Activation

The metinel node material was kept on ice and immediately taken care of using AIM V® Media (Invitrogen) at all times. Single cell suspensions of metinel node lymphocytes was obtained through gentle homogenisation in a loose fit glass homogenisator, and following homogenisation cells were washed twice in medium. The metinel node lymphocytes were put in cell culture flasks at 4 million cells/ml and interleukin-2 (IL-2) (Proleukin®, Chiron) was added to a concentration of 240 IU/ml medium.

Autologous metastasis extract was prepared by homogenisation with an Ultra Turrax in 5 volumes (w/v) 2×PBS followed by denaturation for 5 minutes at 97° C. Three to four days after initiation of the cell culture autologous tumour extract was added at a concentration of 1/100. For long-term culture the cells were kept in a cell incubator at 37° C. and 5% $CO_2$ and 240 IU IL-2/ml media added every 3-4 days.

Phase II, Activation and Expansion

After 18-22 days the cell cultures were monitored for the expression of CD25. When the number of CD25 expressing cells was diminished below 5% the cells were restimulated in Phase II (FIG. 4) by the addition of autologous metastasis extract at a concentration of 1/100. For efficient antigen presentation autologous PBMC were collected using Ficoll-Paque PLUS (Amersham Biosciences, GE Healthcare), radiated with 2500 rad and added to the cell cultures. Three days after restimulation interferon-α (Introna) in conc. 100-500 IU/ml and anti IL-4 antibody was added to a concentration of 2 μg/ml. After 5 to 8 days IL-12 (4 ng/ml) was added to the expansion in order to promote induction of IFN-γ producing Th1 cells.

The day before transfusion to the patient the cell cultures were subject to purification using a Ficoll-Paque PLUS (Amersham Biosciences, GE Healthcare) in order to retrieve the viable cells in the culture. On the day of transfusion the cells were washed twice in Saline solution (Natriumklorid Baxter Viaflo 9 mg/ml, Baxter) and then transferred to a transfer bag containing 100-200 ml of saline solution and 1% Human Serum Albumin (Baxter). Investigations for microbial presence were performed prior to transfusion. Infusions of the cells were performed during 1-2 hours under professional medical supervision.

Immunological Evaluation

Further immunological evaluation was performed using tritium labelled thymidine incorporation proliferation assays. An aliquot of metinel node lymphocytes was set aside for this purpose, a single cell suspension of non-metinel node lymphocytes was obtained by gentle pressure in a loose fit glass homogenisator and peripheral blood leukocytes were purified by Ficoll-Paque PLUS (Amersham Biosciences, GE Healthcare).

Cells were resuspended and washed twice in RPMI 1640 (Life technologies) containing 2.5% fetal calf serum (FCS) (Life technologies). Finally, cells were resuspended in RPMI 1640 proliferation media containing 10% human AB serum (Sigma), 1% penicillin-streptomycin (Sigma) and 1% glutamine (Sigma). Lymph node cells and purified PBL were used at $3 \times 10^5$ cells/well in a 96-well plate and stimulated with metastasis homogenate diluted 1/100, 1/10 or Con A 10 µg/ml (Sigma) in triplicates. Proliferation was measured on day 5, 6 and 7 by adding 1 µCi of $^3$H-Thymidine/well (Amersham) 18 hours prior to harvesting. Samples were subjected to scintillation counting.

At the start of cell culture, stimulations of lymph node cells and PBL, for the measurement of IFN-γ secretion, were performed in 96-well plates with $3 \times 10^5$ cells/well in triplicate with tumour homogenate diluted 1/10 and 1/100, or Con A 10 µg/ml (Sigma). The amount of secreted IFN-γ was measured with ELISA (Human IFN-γ Duoset, R&D Systems) on culture supernatants in pooled samples of the triplicates (FIG. 7). At the end of cell cultures samples of the supernatant was removed and IFN-γ and IL-4 secretion measured in triplicates with ELISA (Human IFN-Duoset and Human IL-4 Duoset, R&D Systems) (FIGS. 8 A and 8 B).

Flow Cytometry Analyses

Characterisation of cells was performed using flow cytometry initially on cells from the metinel node, non-metinel node, PBMC and from the metastasis. From the metinel node acquired lymphocytes in culture samples were taken every two to three weeks for flow cytometry analyses. Cells were incubated for 30 minutes in PBS supplemented with 2% FCS and 0.05% NaN$_3$ (FACS buffer) with antibodies against markers for immune cell subpopulations and for lymphocyte activation (FIGS. 5, 6, and 7). Antibodies conjugated with Fluorescein isothiocyanate (FITC) against the following markers were used: CD69, HLA-DR, CD45RA, CD25, conjugated with phycoerythrin (PE): CD62L, CD19, CD45RO, CD56, conjugated with Peridinin-Chlorophyll-Protein (PerCP): CD8, CD3, conjugated with allophycocyanin (APC): CD4, CD14, CD8.

The Vβ-repertoire was examined using the Beta mark kit (Beckman Coulter), $5 \times 10^5$ cells/tube was stained in 10 µl of the 8 different vials containing mixtures of FITC, PE and dual-colour FITC-PE conjugated TCR Vβ antibodies and with the addition of CD8 PerCP and CD4 APC to each tube. (FIG. 9).

Example 3

Treatment of Metastases by Administering Expanded Metastasis-Reactive T-Lymphocytes The following three cases tend to illustrate that T-lymphocytes obtained and expanded from metinel lymph nodes may be used for treating disseminated cancer.

A 47 year old man had earlier been operated on for a colon cancer in the caecum with a right-sided hemicolectomy. One year later he developed a 5 cm large intraabdominal recurrence in the mesenteric fat outside the area of the anastomosis. During surgery, patent blue dye was injected close in the fat surrounding the metastasis and three metinel nodes along the medial colic artery, including one apical node in the root of the mesentery, were identified. A resection of the anastomotic region and the recurrence was made en bloc. The metinel nodes and an invasive part of the metastasis were dissected postoperatively and processed as described herein. Metastasis-reactive lymphocytes were expanded to high numbers. The patient had a transfusion of these autologous CD4+ T-cells about four weeks after the operation. He has been in perfect health since the operation with normal thoracic and abdominal CT-scans without signs of metastases and normal CEA-level (tumour marker). So far the follow-up after transfusion is 36 months.

A 63 year old woman had been operated on for ovarian cancer with bilateral oophorectomy. At surgery she had disseminated disease to the omentum and went through several tumour-reductive operations, including a resection of the right colon due to a metastasis. One year later she developed a resistance in the left groin and a fine needle biopsy proved a metastasis from ovarian cancer. Lymphoscintigraphy demonstrated two metinel nodes close together distally and medially to the groin lymph node metastasis (see FIG. 1). The lymph node was located with use of technetium-99m and a gamma-ray detection tube, in combination with patent blue dye. The node and metastasis were processed according to the same principles as above. Seven months after treatment the patient is in good health working full time. The tumour marker CA 135 has decreased from high to low numbers.

The third example was a 54 years old man and he had been operated due to low rectal cancer with an abdominoperineal rectal amputation. At surgery a liver metastasis in the left lobe was identified (despite negative liver-scan before operation). After another 6 weeks he was operated on with a left-sided liver resection. Patent blue dye was injected in the parenchyma around the metastasis and after a few minutes two metinel nodes were turning blue in the hepatoduodenal ligament. No metastases were detected in the metinel nodes but they all showed activity against the tumour. The patient was treated with expanded tumour-reactive lymphocytes originating from the metinel nodes. Despite initial treatment with tumour-reactive lymphocytes and good general condition he developed a new liver metastasis in the right liver lobe and a second liver resection was done. At this operation injection of patent blue dye around the 2 cm large metastasis identified 2 metinel nodes located in the hilus of the liver. He was treated again with a transfusion of tumour-reactive lymphocytes derived from the new metinel node. The patient recovered completely and has been working full time. According to CT-images he has some residual disease in the liver and a slightly elevated tumour marker (CEA). The total follow-up since first transfusion of lymphocytes is 36 months.

REFERENCES

Marits P et al. Detection of immune responses against urinary bladder cancer in sentinel lymph nodes. Eur Urol accepted.

Moore K L. Clinically oriented anatomy. Baltimore: Williams and Wilkins. 1985. p 42-p 45.

Renkins E M. Some consequences of capillary permaebility to macromolecules: Starling's hypothesis reconsidered. Am J Physiology. 1986; 250:H706-H710.

Specific Embodiments

1. A method for treating a patient suffering from a disseminated cancer, the method comprising
   i) identifying in a patient one or more metinel lymph nodes,
   ii) resecting the one or more nodes and, optionally all or part of the metastases,
   iii) isolating metastasis-reactive T-lymphocytes from said lymph nodes,
   iv) in vitro expanding said metastasis-reactive T-lymphocytes,
   v) administering the thus obtained T-lymphocytes to the patient,
   wherein the T-lymphocytes are CD4+ helper and/or CD8+ T-lymphocytes.
2. A method according to embodimentembodiment 1, wherein the cancer is any solid neoplasm of epithelial, mesenchymal or embryological origin in any anatomical location, such as for epithelial neoplasms, such as e.g., carcinomas in the breast, colon, pancreas, bladder, small intestines, prostate, cervix, vulva, ovaries; for mesenchymal neoplasms, such as, e.g., sarcomas in the joints, bones, muscles and tendons and some hematological neoplasms such as lymphomas; for embryological neoplasms, such as, e.g., teratomas.
3. A method according to embodiment 1 or 2, wherein the metinel lymph node is identified in step i) by injecting one or more lymph node locators into the patient.
4. A method according to any of the preceding embodiments, wherein the one or more lymph node locators are affinity based.
5. A method according to any of embodiments 1-4, wherein the one or more lymph node locators are non-affinity based.
6. A method according to any of the preceding embodiments wherein one or more lymph node locators are injected into, above, around, adjacent and/or under the metastasis.
7. A method according to any of the preceding embodiments, wherein the one or more lymph node locators are injected by a single injection.
8. A method according to any of embodiments 1-6, wherein the one or more lymph node locators are injected by multiple injections.
9. A method according to any of the preceding embodiments, wherein the one or more lymph node locators are injected by a non-surgical procedure.
10. A method according to any of embodiments 1-9, wherein the one or more lymph node locators are injected as part of a surgical procedure.
11. A method according to any of the preceding embodiments wherein the in vitro expansion step iv) comprises
   i) a first phase of stimulating tumour-reactive CD4+ helper and/or CD8+T-lymphocytes with tumour-derived antigen together with at least one substance having agonistic activity towards the IL-2 receptor to promote survival of tumour-reactive CD4+ helper and/or CD8+ T-lymphocytes, and
   ii) a second phase of activating and promoting growth of tumour-reactive CD4+ helper and/or CD8+ T-lymphocytes, wherein the second phase ii) is initiated when the CD25 cell surface marker (or IL-2R marker) is down-regulated on T-lymphocytes.
12. A method according to embodiment 11, wherein the down-regulation is defined as that 5% or less of the T-lymphocyte population expresses CD25.
13. A method according to embodiment 11 or 12, wherein the T-lymphocytes are present in a culture medium.
14. A method according to embodiment 13, wherein the culture medium is a serum-free medium, such as, e.g. AIMV medium.
15. A method according to any of the preceding embodiments, wherein the first phase i) is initiated by adding the at least one substance having agonistic activity towards the IL-2 receptor.
16. A method according to embodiment 15, wherein the substance having agonistic activity towards the IL-2 receptor is IL-2.
17. A method according to embodiment 16, wherein IL-2 is added in a low dose, such as, e.g., from about 100 IU/ml culture medium to about 700 IU/ml culture medium, from about 100 IU/ml culture medium to about 600 IU/ml culture medium, from about 100 IU/ml culture medium to about 500 IU/ml culture medium, from about 100 IU/ml culture medium to about 400 IU/ml culture medium, from about 100 IU/ml culture medium to about 300 IU/ml culture medium and from about 100 IU/ml culture medium to about 200 IU/ml culture medium.
18. A method according to any of the preceding embodiments, wherein a further amount of the at least one substance having agonistic activity towards the IL-2 receptor is added regularly throughout phase i), such as, e.g., every $2^{nd}$, $3^{rd}$ or $4^{th}$ day of phase i).
19. A method according to embodiment 18, wherein the substance having agonistic activity towards the IL-2 receptor is IL-2.
20. A method according to embodiment 19, wherein the concentration of IL-2 added is from about 100 IU/ml culture medium to about 700 IU/ml culture medium, from about 100 IU/ml culture medium to about 600 IU/ml culture medium, from about 100 IU/ml culture medium to about 500 IU/ml culture medium, from about 100 IU/ml culture medium to about 400 IU/ml culture medium, from about 100 IU/ml culture medium to about 300 IU/ml culture medium and from about 100 IU/ml culture medium to about 200 IU/ml culture medium.
21. A method according to any of the preceding embodiments, wherein the tumour-derived antigen is added from day 2 to and including day 5 of the first phase i), such as, e.g., on day 2, on day 3, on day 4 or on day 5.
22. A method according to any of embodiments 11-20, wherein the tumour-derived antigen is added essentially at the same time as when phase i) is initiated or at the most up to 3 days thereafter.
23. A method according to any of the preceding embodiments, wherein the tumour-derived antigen is a denatured homogenate of a tumour.
24. A method according to any of the preceding embodiments, wherein the tumour-derived antigen is a protein, polypeptide or peptide.
25. A method according to any of the preceding embodiments, wherein the second phase ii) is initiated from day 17 to and including day 23 of the first phase i), such as, e.g. on day 17, on day 18, on day 19, on day 20, on day 21, on day 22 or on day 23.
26. A method according to any of the preceding embodiments, wherein the second phase is initiated by the addition of tumour-derived antigen to the T-lymphocytes for activating tumour-reactive CD25-negative T-lymphocytes.
27. A method according to embodiment 26, wherein the tumour-derived antigen is a denatured homogenate of a tumour.

28. A method according to embodiment 26, wherein the tumour-derived antigen is a tumour protein, polypeptide or peptide.
29. A method according to any of embodiments 26-28, which further comprises addition to the T-lymphocytes of antigen presenting cells together with the tumour-derived antigen.
30. A method according to embodiment 20, wherein the antigen presenting cells are irradiated peripheral blood leucocytes containing antigen-presenting B-cells and/or monocytes.
31. A method according to any of the preceding embodiments, wherein the second phase ii) comprises adding at least one substance capable of up-regulating IL-12R on the T-lymphocytes.
32. A method according to embodiment 31, wherein the substance(s) capable of up-regulating IL-12R on the T-lymphocytes is substance(s) having agonistic activity towards an interferon receptor.
33. A method according to embodiment 32, wherein the substance(s) having agonistic activity towards an interferon receptor is an interferon.
34. A method according to embodiment 33, wherein the substance(s) having agonistic activity towards an interferon receptor is interferon-$\alpha$.
35. A method according to any of embodiments 31-34, wherein the substance(s) capable of up-regulating IL-12R on the T-lymphocytes, such as, e.g. a substance having agonistic activity towards an interferon receptor, is added when the level of IL-12 is at least 1 fold, such as, e.g., at least 2, at least 3 fold, at least 4 fold, or at least 5 fold increased as compared to the level of IL-12 on day 1 of phase ii).
36. A method according to any of embodiments 31-35, wherein the substance capable of up-regulating IL-12R on the T-lymphocytes, such as, e.g. a substance having agonistic activity towards an interferon receptor is added from day 2 to and including day 4 after initiating the second phase ii), such as, e.g. on day 2, on day 3 or on day 4.
37. A method according to any of the preceding embodiments, wherein the second phase ii) comprises adding one or more substances capable of antagonizing development of Th2 type T -lymphocytes.
38. A method according to embodiment 37, wherein the one or more substances capable of antagonizing development of Th2 type T-lymphocytes are one or more substances capable of neutralizing IL-4, IL-5, IL-10, and/or TGF-beta.
39. A method according to embodiment 38, wherein the one or more substances capable of neutralizing IL-4, IL-5, IL-10, and/or TGF-beta are anti IL-4 antibody, anti IL-5 antibody and/or anti IL-10 antibody.
40. A method according to any of embodiments 37-39, wherein the one or more substances capable of antagonizing development of Th2 type T-lymphocytes, such as, e.g., one or more substances capable of neutralizing IL-4, IL-5, IL-10, and/or TGF-beta is added on day 1 of the second phase ii).
41. A method according to any of embodiments 37-39, wherein the one or more substances capable of antagonizing development of Th2 type T-lymphocytes, such as, e.g., one or more substance capable of neutralizing IL-4, IL-5, IL-10, and/or TGF-beta is added in a subsequent step after addition of the substance capable of up-regulating IL-12R on the T-lymphocytes.
42. A method according to embodiment 41, wherein the one or more substances capable of antagonizing development of Th2 type T-lymphocytes, such as, e.g., one or more substance capable of neutralizing IL-4, IL-5 and/or IL-10 is added one day after addition of the substance capable of up-regulating IL-12R on the T-lymphocytes.
43. A method according to any of the preceding embodiments, wherein a further amount of the one or more substance capable of antagonizing development of Th2 type T-lymphocytes, such as, e.g., one or more substance capable of neutralizing IL-4, IL-5, IL-10 and/or TGF-beta is added regularly throughout phase ii).
44. A method according to embodiment 43, wherein a further amount of the one or more substance capable of antagonizing development of Th2 type T-lymphocytes, such as, e.g., one or more substance capable of neutralizing IL-4, IL-5, IL-10 and/or TGF-beta is added every $2^{nd}$, $3^{rd}$ or $4^{th}$ day of phase ii).
45. A method according to any of the preceding embodiments, wherein a further amount of a substance having agonistic activity towards the IL-2 receptor is added regularly throughout phase ii).
46. A method according to embodiment 45, wherein the substance having agonistic activity towards the IL-2 receptor is added every $2^{nd}$, $3^{rd}$ or $4^{th}$ day of phase ii), such as, e.g., every $3^{rd}$ day.
47. A method according to embodiment 45 or 46, wherein the substance having agonistic activity towards the IL-2 receptor is IL-2.
48. A method according to any of the preceding embodiments, wherein the second phase ii) comprises adding one or more substances promoting the development of Th1 type T -lymphocytes.
49. A method according to embodiment 48, wherein the one or more substances promoting the development of Th1 type T-lymphocytes is substances having agonistic activity towards the IL-7, IL-12, IL-15 and/or IL-21 receptor.
50. A method according to embodiment 49, wherein the one or more substances is selected from IL-7, IL-12, IL-15 and IL-21.
51. A method according to any of embodiments 48-50, wherein one or more substances promoting the development of Th1 type T-lymphocytes, such as, e.g., substances having agonistic activity towards the IL-7, IL-12, IL-15 and/or IL-21 receptor is added when the level of IFN-gamma is increased as compared to the level of IFN-gamma on initiation of second phase ii).
52. A method according to embodiment 51, wherein the increased level of IFN-gamma is determined as at least a 1 fold increase in IFN-gamma level, such as, e.g., at least a 2 fold, at least a 3 fold, at least a 4 fold increase as compared to the level of IFN-gamma on initiation of the second phase ii).
53. A method according to any of embodiments 48-52, wherein the one or more substances promoting the development of Th1 type T-lymphocytes, such as, e.g., substances having agonistic activity towards the IL-12, IL-15 and/or IL-21 receptor is added when CD25 and/or CD69 are down-regulated.
54. A method according to any of embodiments 48-53, wherein the concentration of each of the one or more substances promoting the development of Th1 type T-lymphocytes, such as, e.g., substances having agonistic activity towards the IL-7, IL-12, IL-15 and/or IL-21 receptor added is from about 150 IU/ml culture medium to about 300 IU/ml culture medium, such as, e.g. 250 IU/ml culture medium.
55. A method according to any of embodiment 48-54, wherein the one or more substances promoting the development of Th1 type T-lymphocytes, such as, e.g., substances having agonistic activity towards the IL-12, IL-15 and/or IL-21 receptor is added from day 5 to and including day 8 after initiating the second phase ii), such as, on day 5, day 6, day 7 or day 8.
56. A method according to any of the preceding embodiment for the preparation of CD4+ helper T-lymphocytes.
57. A method according to any of the preceding embodiments for the preparation of effector T-lymphocytes.
58. A method according to any of the preceding embodiments for the preparation of memory T-lymphocytes.
59. A method according to any of the preceding embodiments for the preparation of Th1 type T-lymphocytes.
60. A method according to any of the preceding embodiments, which further comprises monitoring the expression of cell surface markers, such as, e.g., CD25 and/or CD69 on the T-lymphocytes continuously during the first phase i) and second phase ii).
61. A method according to embodiment 60, wherein the T-lymphocytes are harvested when CD25 on T-lymphocytes in the second phase ii) is down-regulated.
62. A method according to embodiment 61, wherein the T-lymphocytes are subjected to at least one additional round of phase ii), when CD25 on T-lymphocytes is down-regulated.
63. A method according to embodiment 61 or 62, wherein the down-regulation is defined as that 5% or less of the CD4 positive T-lymphocyte population expresses CD25.
64. A method according to any of the preceding embodiments, wherein the tumour-reactive T-lymphocytes are harvested from day 10 to and including day 14 after initiating the second phase ii).
65. A method according to embodiment 64, wherein the tumour-reactive T-lymphocytes are purified after harvest.
66. A method according to any of the preceding embodiments further comprising a step of freezing the tumour-reactive T-lymphocytes obtained in the second phase ii).
67. A method according to any of the preceding embodiments, wherein the T-lymphocytes are derived from lymph nodes draining a primary tumour and/or a metastasis, or they are derived from blood.
68. A method according to any of the preceding embodiments, wherein the tumour-reactive T-lymphocytes in step iv) are administered intravenously, intraarterially or intrathecally, intraperitonally.
69. A method according to any of the preceding embodiments, wherein the amount of tumour-reactive T-lymphocytes administered is at least 10 million, such as, e.g. at least 20 million, at least 30 million, at least 40 million, at least 50 million, at least 60 million, at least 70 million or at least 80 million.
70. A method according to any the preceding embodiments, wherein the tumour-reactive T -lymphocytes administered are a combination of effector T-lymphocytes and memory T-lymphocytes.
71. A method according to embodiment 70, wherein the percentage of effector T-lymphocytes is from about 10% to about 65%, such as, e.g., from about 20% to about 50% or from about 30% to about 40%.
72. A method according to any of the preceding embodiments, wherein the tumour-reactive T-lymphocytes are autologous.
73. A method according to any of the preceding embodiments, wherein the tumour-reactive T-lymphocytes are non-autologous.

T cells
74. A tumour-reactive T-lymphocyte prepared according to the method defined in any of embodiments 1-73.
75. A tumour-reactive T-lymphocyte according to embodiment 74, which is a CD4+T-lymphocyte.
76. A tumour-reactive T-lymphocyte according to embodiment 74 or 75, which is an effector T-lymphocyte.
77. A tumour-reactive T-lymphocyte according to any of embodiments 74-76, which is a memory T-lymphocyte.
78. A tumour-reactive T-lymphocyte according to any of embodiment 74-77, which is a Th1 type T-lymphocyte.
79. Use of tumour-reactive T-lymphocytes according to any of embodiments 74-78, for the preparation of a medicament for the treatment of disseminated cancer.
80. Kit for use in a method according to any of embodiments 1-73, the kit comprising a media for cultivation of T-lymphocytes.
81. Kit according to embodiment 80 further comprising one or more substances for stimulating, activating and directing tumour-reactive T-lymphocytes.
82. Kit according to embodiment 80 or 81, wherein the media a serum free medium, such as, e.g. AIMV, RPMI 1640, DMEM or MEM.
83. Kit according to any of embodiments 80-82, wherein the one or more substances for stimulating, activating an directing tumour-reactive T-lymphocytes are selected from tumour -derived antigen, substances having agonistic activity towards the IL-2 receptor, substances capable of up-regulating IL-12R on the T-lymphocytes, substances capable of antagonizing development of Th2 type T-lymphocytes and substances promoting the development of Th1 type T-lymphocytes.
84. Kit according to any of embodiments 80-83, wherein the one or more substances for stimulating, activating and directing tumour-reactive T-lymphocytes are selected from the group comprising IL-2, interferon-alpha, anti-IL-4 antibody, anti-IL-5 antibody, anti-IL-10 antibody, IL-7, IL-12, IL-15 and IL-21.
85. Kit according to any of embodiments 80-84, comprising a pharmaceutical composition suitable for intravenous administration.
86. A kit for detection of metinel lymph nodes, the kit comprising a syringe and a lymph node locator.
87. A kit for detection of metinel lymph nodes, the kit comprising a syringe prefilled with a lymph node locator.
88. Kit according to any of embodiments 80-87 further comprising instructions for use.
89. Kit according to embodiment 88, wherein the instructions are in the form of computer software.

The invention claimed is:
1. A method for treating a patient suffering from a disseminated cancer, the method comprising:
   i) identifying in a patient one or more metinel lymph nodes, and, optionally, identifying all or part of metastases of the disseminated cancer;
   ii) resecting the one or more nodes and, optionally, all or part of the metastases;
   iii) isolating metastasis-reactive T-lymphocytes from said lymph nodes;
   iv) in vitro expanding said metastasis-reactive T-lymphocytes; and
   v) administering the thus obtained T-lymphocytes to the patient,
   wherein the T-lymphocytes are CD4+helper or CD8+T-lymphocytes.
2. A method according to claim 1, wherein the in vitro expansion step comprises:
   (a) a first phase of stimulating tumour-reactive CD4+ helper or CD8+T-lymphocytes with tumour-derived antigen together with at least one substance having ago- nistic activity towards the IL-2 receptor to promote survival of tumour-reactive CD4+helper or CD8+T-lymphocytes; and (b) a second phase of activating and promoting growth of tumour-reactive CD4+helper or CD8+T-lymphocytes, wherein the second phase is initiated when the CD25 cell surface marker or IL-2R marker is down-regulated on T-lymphocytes.

3. A method according to claim 2, wherein the down-regulation is defined as that 5% or less of the T-lymphocyte population expresses CD25.

4. A method according to claim 3, wherein the first phase is initiated by adding the at least one substance having agonistic activity towards the IL-2 receptor.

5. A method according to claim 4, wherein the substance having agonistic activity towards the IL-2 receptor is IL-2.

6. A method according to claim 2, wherein the tumour-derived antigen is a denatured homogenate of a tumour.

7. A method according to claim 2, wherein the second phase is initiated by the addition of tumour-derived antigen to the T-lymphocytes for activating tumour-reactive CD25-negative T-lymphocytes.

8. A method according to claim 7, which further comprises addition of antigen presenting cells to the T-lymphocytes together with the tumour-derived antigen.

9. A method according to claim 8, wherein the antigen presenting cells are irradiated peripheral blood leucocytes containing antigen-presenting B-cells and/or monocytes.

10. A method according to claim 2, wherein the second phase comprises adding at least one substance capable of up-regulating IL-12R on the T-lymphocytes.

11. A method according to claim 2, wherein the second phase comprises adding one or more substances capable of antagonizing development of Th2 type T-lymphocytes.

12. A method according to claim 11, wherein the one or more substances capable of antagonizing development of Th2 type T-lymphocytes are one or more substances capable of neutralizing IL-4, IL-5, IL-10, or TGF-beta.

13. A method according to claim 12, wherein the one or more substances capable of neutralizing IL-4, IL-5, IL-10, or TGF-beta are anti IL-4 antibody, anti IL-5 antibody or anti IL-10 antibody.

14. A method according to any of the claim 2, 12 or 13, wherein a further amount of the one or more substance capable of antagonizing development of Th2 type T-lymphocytes is added regularly throughout phase.

15. A method according to claim 2, wherein the second phase comprises adding one or more substances promoting the development of Th1 type T-lymphocytes.

16. A method according to claim 15, wherein the one or more substances promoting the development of Th1 type T-lymphocytes is substances having agonistic activity towards the IL-7, IL-12, IL-15 or IL-21 receptor.

17. A method according to claim 16, wherein the one or more substances is selected from IL-7, IL-12, IL-15 and IL-21.

18. A method according to either of claim 1 or 2 for the preparation of Th1 type T-lymphocytes of the memory or effector type 19. A method according to claim 2, which further comprises monitoring the expression of cell surface markers continuously during the first phase and second phase, and wherein the T-lymphocytes are harvested when CD25 on T-lymphocytes in the second phase is down-regulated.

20. A method according to claim 19, wherein the T-lymphocytes are subjected to at least one additional round of the second phase, when CD25 on T-lymphocytes is down-regulated.

21. A method according to claim 1 or 2, wherein the T-lymphocytes are derived from metinel lymph nodes draining a metastasis, or they are derived from blood.

22. A method according to claim 2, wherein the tumour-derived antigen is autologous tumour-derived antigen.

23. A method according to claim 2, wherein the tumour-derived antigen is autologous denatured tumour extract.

24. A method for treating a patient suffering from a disseminated cancer, the method comprising administering T-lymphocytes to the patient, wherein the T-lymphocytes are CD4+helper or CD8+T-lymphocytes and are obtained by:
   i) identifying in a patient one or more metinel lymph nodes, and, optionally, identifying all or part of metastases of the disseminated cancer;
   ii) resecting the one or more nodes and, optionally, all or part of the metastases;
   iii) isolating metastasis-reactive T-lymphocytes from said lymph nodes; and
   iv) in vitro expanding said metastasis-reactive T-lymphocytes by a method comprising:
      (a) a first phase of stimulating tumour-reactive CD4+ helper or CD8+T-lymphocytes with tumour-derived antigen together with at least one substance having agonistic activity towards the IL-2 receptor to promote survival of tumour-reactive CD4+helper or CD8+T-lymphocytes; and
      (b) a second phase of activating and promoting growth of tumour-reactive CD4+helper or CD8+T-lymphocytes, wherein the second phase is initiated when the CD25 cell surface marker or IL-2R marker is down-regulated on T-lymphocytes.

* * * * *

UNITED STATES PATENT AND TRADEMARK OFFICE
CERTIFICATE OF CORRECTION

Page 1 of 1

PATENT NO. : 8,211,425 B2
APPLICATION NO. : 12/158687
DATED : July 3, 2012
INVENTOR(S) : Ola Winqvist and Magnus Thörn It is certified that error appears in the above-identified patent and that said Letters Patent is hereby corrected as shown below:

Claim 14, Column 29, line 43, change "claim" to --claims--

Signed and Sealed this
Eighteenth Day of September, 2012

David J. Kappos
*Director of the United States Patent and Trademark Office*